United States Patent
Castellon

(10) Patent No.: US 7,101,707 B2
(45) Date of Patent: Sep. 5, 2006

(54) SECONDARY SPROUTING FOR ISOLATION AND EXPANSION OF ENDOTHELIAL SPROUT CELLS AND ENDOTHELIAL PRECURSOR CELLS FROM A MIXED POPULATION AND FOR SCREENING SUBSTANCES

(75) Inventor: Raquel Castellon, Norwalk, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 371 days.

(21) Appl. No.: 10/328,812

(22) Filed: Dec. 23, 2002

(65) Prior Publication Data

US 2004/0121457 A1 Jun. 24, 2004

(51) Int. Cl.
C12N 5/00 (2006.01)
C12N 5/02 (2006.01)

(52) U.S. Cl. .................. 435/375; 435/377; 435/383

(58) Field of Classification Search ............... 435/375, 435/377, 383
See application file for complete search history.

(56) References Cited

U.S. PATENT DOCUMENTS 5,886,026 A 3/1999 Hunter et al.

OTHER PUBLICATIONS

Castellon et al ., Invest Ophtalmol.Vis.Sci, Aug. 2002, vol. 43, pp. 2758-2766.*
Aiello, L. P. et al., *Role of vascular endothelial growth factor in diabetic vascular complications*, Kidney Int. vol. 58 Suppl. 77 , pp. S113-S119 (2000).
Aiello, L. P., *Vascular Endothelial Growth Factor and the Eye: Biochemical Mechanisms of Action and Implications for Novel Therapies*, Ophthalmic Res. vol. 29, No. 5, pp. 354-362 (1997).
Aiello, L. P. et al., *Vascular endothelial growth factor-induced retinal permeability is mediated by protein kinase C in vivo and suppressed by an orally effective beta-isoform-selective inhibitor*, Diabetes 46(9):1473-80 (Sep. 1997). Abstract Only.
Albini, A, *Tumor and Endothelial Cell Invasion of Basement Membranes*, Pathol. Oncol. Res. vol. 4, No. 3, pp. 230-241 (1998).
Al-Nedawi, K.N. et al., *Interferon gamma bound to endothelial cells is phosphorylated by ecto-protein kinases*, Acta Biochim Pol 46(3):693-702 (1999). Abstract Only.
Asahara, T. et al., *Isolation of Putative Progenitor Endothelial Cells for Angiogenesis*, Science vol. 275, No. 5302, pp. 964-967 (Feb. 1997).

Baatout, S., *Endothelial Differentiation Using Matrigel (review)*, Anticancer Res. vol. 17, No. 1A, pp. 451-455 (1997).
Benelli, R. et al., *In vitro models of angiogenesis: the use of Matrigel*, Int. J. Biol Markers vol. 14, No. 4, pp. 243-246 (1999).
Bikfalvi, A. et al., *Biological Roles of Fibroblast Growth Factor-2*, Endocrine Reviews vol. 18, No. 1, pp. 26-45 (1997).
Borgstrom, P. et al., *Importance of VEGF for breast cancer angiogenesis in vivo: implications from intravital microscopy of combination treatments with an anti-VEGF neutralizing monoclonal antibody and doxorubicin*, Anticancer Res. 19(5B):4203-14 (Sep.-Oct. 1999). Abstact Only.
Boulton, M. et al., *Intravitreal growth factors in proliferative diabetic retinopathy: correlation with neovascular activity and glycaemic management*, British J. of Ophthalmology vol. 81, pp. 228-233 (Mar. 1997).
Campochiaro, P. A., *Retinal and Choroidal Neovascularization*, J. Cell Physiol, vol. 184, pp. 301-310 (Sep. 2000).
Carmeliet, P. et al., *Angiogenesis in cancer and other diseases*, Nature vol. 407, No. 6801, pp. 249-257 (Sep. 2000).
Castellon, R. et al., *Effects of Angiogenic Growth Factor Combinations on Retinal Endothelial Cells*, Exp. Eye Res. vol. 74, pp. 523-535 (2002).
Choi, K. et al., *A common precursor for hematopoietic and endothelial cells*, Development vol. 125, pp. 725-732 (1998).
Ferrara, N. et al., *The Biology of Vascular Endothelial Growth Factor*, Endocrine Reviews vol. 18, No. 1, pp. 4-25 (1997).
Freyberger, H. et al., *Increased levels of platelet-derived growth factor in vitreous fluid of patients with proliferative diabetic retinopathy*, Exp. Clin. Endocrinol. Diabetes 108(2):106-9 (2000). Abstract Only.
Fujimoto, J. et al., *Angiogenesis in Endometriosis and Angiogenic Factors*, Gynecol Obstet Invest. vol. 48, Suppl. 1, pp. 14-20 (1999).
Gazvani, R. et al., *New considerations for pathogenesis of endometriosis*, Int. J. Gynaecol Obstet vol. 76, No. 2, pp. 117-126 (Feb. 2002).

(Continued)

Primary Examiner—Christina Chan
Assistant Examiner—Michail A. Belyavskyi
(74) Attorney, Agent, or Firm—Jones Day

(57) ABSTRACT

In vitro methods are disclosed that rely on a novel phenomenon of secondary sprouting by cultured endothelial precursor cells, after angiogenic-like tube formation and collapse have occurred on a basement membrane matrix. Particularly disclosed is an in vitro method of isolating and expanding, from a mixed population of mammalian cells originating from a tissue sample, a cellular population enriched for endothelial sprout cells, including cells having one or more physiological and/or immunological features of endothelial precursor cells. Also disclosed is an in vitro method for a screening a substance for potential proangiogenic or anti-angiogenic activity.

12 Claims, 13 Drawing Sheets

OTHER PUBLICATIONS

Gazvani, R. et al., *Peritoneal environment, cytokines and angiogenesis in the pathophysiology of endometriosis*, Reproduction vol. 123, No. 2, pp. 217-226 (Feb. 2002).

Goto, F. et al., *Synergistic Effects of Vascular Endothelial Growth Factor and Basic Fibroblast Growth Factor on the Proliferation and Cord Formation of Bovine Capillary Endothelial Cells Within Collagen Gels*, Lab Invest. vol. 69, No. 5, pp. 508-517 (1993).

Hata, Y. et al., *Basic Fibroblast Growth Factor Induces Expression of VEGF Receptor KDR Through a Protein Kinase C and p44/p42 Mitogen-Activated Protein Kinase-Dependent Pathway*, Diabetes vol. 48, pp. 1145-1155 (May 1999).

Healy, D. L. et al., *Angiogenesis: a new theory for endometriosis*, Hum Reprod Update vol. 4, No. 5, pp. 736-740 (1998).

Horak, E.R. et al., *Angiogenesis, assessed by platelet/endothelial cell adhesion molecule antibodies, as indicator of node metastases and survival in breast cancer*, Lancet 340(8828):1120-4 (Nov. 1992). Abstract Only.

Kleinman, H. K. et al., *Isolation and Characterization of Type IV Procollagen, Laminin, and Heparan Sulfate Proteoglycan from the EHS Sarcoma*, Biochemistry vol. 21, No. 24, pp. 6188-6193 (1982).

Linderholm, B. et al., *Vascular endothelial growth factor is of high prognostic value in node-negative breast carcinoma*, J. Clin Oncol. 16(9):3121-8 (Sep. 1998). Abstract Only.

Ljubimov, A. V. et al., *Basement Membrane Abnormalities in Human Eyes with Diabetic Retinopathy*, J. Histochem Cytochem. vol. 44, No. 12, pp. 1469-1479 (1996).

Matsumoto, K. et al., *In Vitro Proliferation Potential of AC133 Positive Cells in Peripheral Blood*, Stem Cells vol. 18, No. 3, pp. 196-203 (May 2000).

Matsuzaki, S. et al., *Angiogenesis in endometriosis*, Gynecol. Obstet. Invest. 46(2):111-5 (Aug. 1998). Abstract Only.

Mayani, H. et al., *Biology of Human Umbilical Cord Blood-Derived Hematopoietic Stem/Progenitor Cells*, Stem Cells vol. 16, No. 3, pp. 153-165 (May 1998).

Miele, C. et al., *Insulin and Insulin-like Growth Factor-I Induce Vascular Endothelial Growth Factor mRNA Expression via Different Signaling Pathways*, J. Biol. Chem. vol. 275, No. 28, pp. 21695-21702 (Jul. 2000).

Ohneda, O. et al., *ALCAM (CD166): its role in hematopoietic and endothelial development*, Blood vol. 98, No. 7, pp. 2134-2142 (Oct. 2001).

Okuda, T. et al., *RUNX1/AML1: A Central Player in Hematopoiesis*, Int. J. Hematol vol. 74, No. 3, pp. 252-257 (May 2001).

Orkin, S. H. et al., *Hematopoiesis and stem cells: plasticity versus developmental heterogeneity*, Nat. Immunol. vol. 3, No. 4, pp. 323-328 (Apr. 2002).

Ozaki, H. et al., *Blockade of Vascular Endothelial Cell Growth Factor Receptor Signaling Is Sufficient to Completely Prevent Retinal Neovascularization*, The Amer. J. of Pathology vol. 156, pp. 697-707 (2000).

Pollman, M. J. et al., *Endothelial Cell Apoptosis in Capillary Network Remodeling*, J. Cell Physiol. vol. 178, pp. 359-370 (1999).

Relf, M. et al., *Expression of the angiogenic factors vascular endothelial cell growth factor, acidic and basic fibroblast growth factor, tumor growth factor beta-1, platelet-derived endothelial cell growth factor, placenta growth factor, and pleiotrophin in human primary breast cancer and its relation to angiogenesis*, Cancer Res. 57(5):963-9 (Mar. 1997). Abstract Only.

Reyes, M. et al., *Origin of endothelial progenitors in human postnatal bone marrow*, J. Clin. Invest. vol. 109, No. 3, pp. 337-346 (Feb. 2002).

Sato, Y., *Molecular mechanism of angiogenesis Transcription factors and their therapeutic relevance*, Pharmacol Ther. vol. 87, pp. 51-60 (Jul. 2000).

Seghezzi, G. et al., *Fibroblast Growth Factor-2 (FGF-2) Induces Vascular Endothelial Growth Factor (VEGF) Expression in the Endothelial Cells of Forming Capillaries: An Autocrine Mechanism Contributing to Angiogenesis*, J. Cell Biol vol. 141, No. 7, pp. 1659-1673 (Jun. 1998).

Smith, L. E. et al., *Regulation of vascular endothelial growth factor-dependent retinal neovascularization by insulin-like growth factor-1 receptor*, Nat. Med. 5(12):1390-5 (Dec. 1999). Abstract Only.

Spirin, K.S. et al., *Basement membrane and growth factor gene expression in normal and diabetic human retinas*, Curr Eye Res. vol. 18, No. 6, pp. 490-499 (1999).

Stavri, G. et al., *Basic Fibroblast Growth Factor Upregulates the Expression of Vascular Endothelial Growth Factor in Vascular Smooth Muscle Cells*, Circulation vol. 92, pp. 11-14 (1995).

Stavri, G. T. et al., *Hypoxia and platelet-derived growth factor-BB synergistically upregulate the expression of vascular endothelial growth factor in vascular smooth muscle Cells*, FEBS Lett. 358(3):311-5 (Jan. 1995). Abstract Only.

Takahashi, Y. et al., *Expression of vascular endothelial growth factor and its receptor, KDR, correlates with vascularity, metastasis, and proliferation of human colon cancer*, Cancer Res. 55(18):3964-8 (Sep. 1995). Abstract Only.

Taylor, R. N. et al., *Angiogenic Factors in Endometriosis*, Ann. N Y Acad. Sci. vol. 955, pp. 89-100; discussion pp. 118, 396-406 (Mar. 2002).

Taylor, R. N. et al., *Endocrine and paracrine regulation of endometrial angiogenesis*, Ann. N Y Acad. Sci. 943:109-21 (Sep. 2001). Abstract Only.

Vukicevic, S. et al., *Identification of Multiple Active Growth Factors in Basement Membrane Matrigel Suggests Caution in Interpretation of Cellular Activity Related to Extracellular Matrix Components*, Exp. Cell. Res. vol. 202, pp. 1-8 (1992).

Weidner, N. et al., *Tumor angiogenesis: a new significant and independent prognostic indicator in early-stage breast carcinoma*, J. Natl. Cancer Inst. 84(24):1875-87 (Dec. 1992). Abstract Only.

Williams, S., *EDITORIAL—Angiogenesis in Three-Dimensional Cultures*, Lab Invest. vol. 69, No. 5, pp. 491-493 (1993).

\* cited by examiner

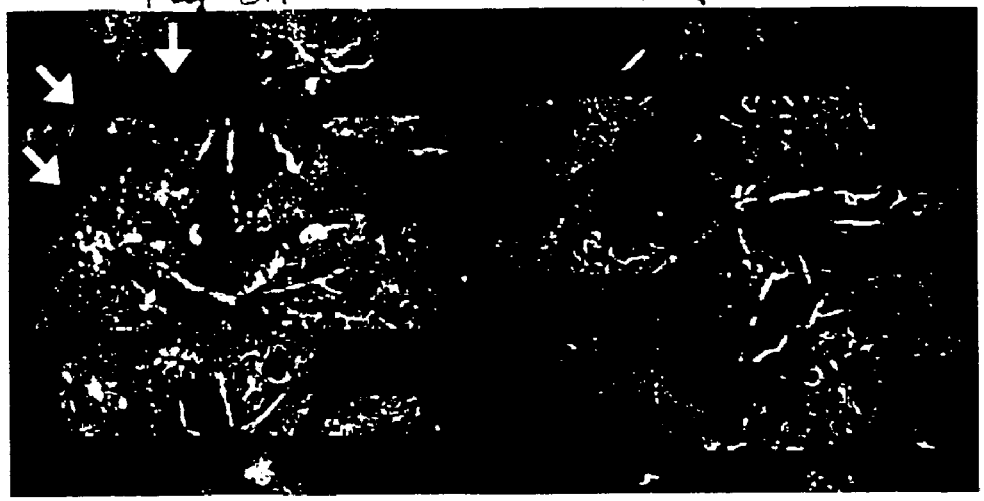
Vehicle　　　　　　Emodin-treated
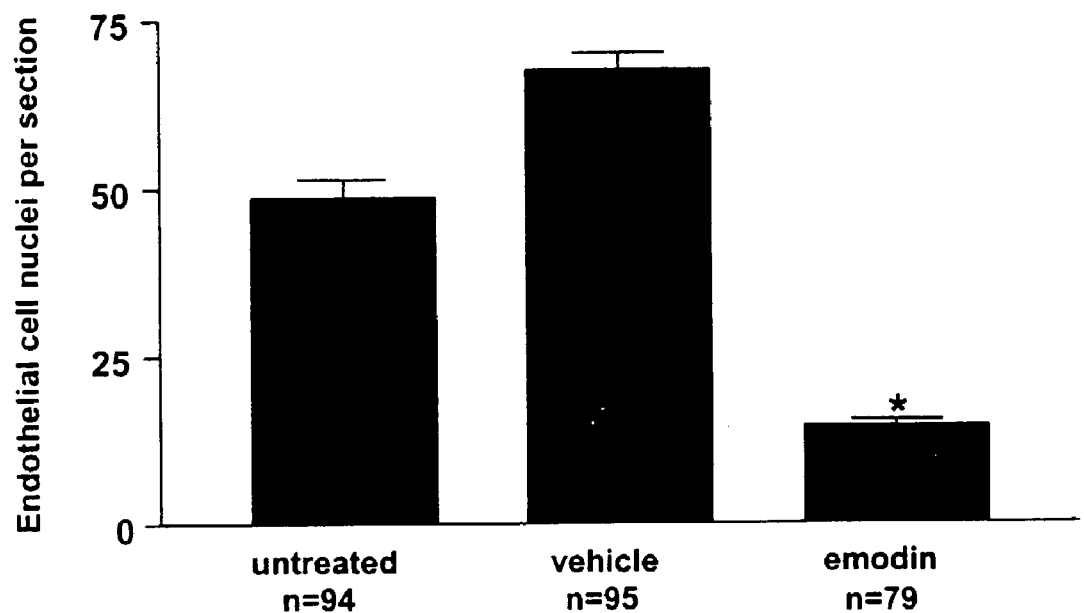
Fig. 7

SEQUENCE LISTING

<160> NUMBER OF SEQ ID NOS: 10

<210> SEQ ID NO 1
<211> LENGTH: 32
<212> TYPE: DNA
<213> ORGANISM: Artificial Sequence
<220> FEATURE:
<223> OTHER INFORMATION: AML-1 forward primer

<400> SEQUENCE: 1
cgtagatgcc agcacgagcc gccgcttcac gc           32

<210> SEQ ID NO 2
<211> LENGTH: 29
<212> TYPE: DNA
<213> ORGANISM: Artificial Sequence
<220> FEATURE:
<223> OTHER INFORMATION: AML-1 reverse primer

<400> SEQUENCE: 2
cgggcttggt ctgatcatct agtttctgc              29

```
<210> SEQ ID NO 3
<211> LENGTH: 31
<212> TYPE: DNA
<213> ORGANISM: Artificial Sequence
<220> FEATURE:
<223> OTHER INFORMATION: AC166 (ALCAM) forward primer

<400> SEQUENCE: 3
cctacagagc aggtgacaat acaagtgctg c                              31

<210> SEQ ID NO 4
<211> LENGTH: 30
<212> TYPE: DNA
<213> ORGANISM: Artificial Sequence
<220> FEATURE:
<223> OTHER INFORMATION: AC166 (ALCAM) reverse primer

<400> SEQUENCE: 4
catagtttcc agcatcctga taatgaagac                                30

<210> SEQ ID NO 5
<211> LENGTH: 32
<212> TYPE: DNA
<213> ORGANISM: Artificial Sequence
<220> FEATURE:
<223> OTHER INFORMATION: CD-34 forward primer

<400> SEQUENCE: 5
tgctcctggc ccagtctgag gtgaggcctc ag                             32

<210> SEQ ID NO 6
<211> LENGTH: 35
<212> TYPE: DNA
<213> ORGANISM: Artificial Sequence
<220> FEATURE:
<223> OTHER INFORMATION: CD-34 reverse primer

<400> SEQUENCE: 6
gctgaatggc cgtttctgga ggtggcctgg ccggt                          35

<210> SEQ ID NO 7
<211> LENGTH: 28
<212> TYPE: DNA
<213> ORGANISM: Artificial Sequence
<220> FEATURE:
<223> OTHER INFORMATION: AC-133 forward primer 1

<400> SEQUENCE: 7
tccaacaccg gaggcgtctt cctcatgg                                  28

<210> SEQ ID NO 8
<211> LENGTH: 34
<212> TYPE: DNA
<213> ORGANISM: Artificial Sequence
<220> FEATURE:
<223> OTHER INFORMATION: AC-133 reverse primer

<400> SEQUENCE: 8
cagataatgt tcaaaatatc ctattattgt tctc                           34

<210> SEQ ID NO 9
<211> LENGTH: 34
<212> TYPE: DNA
<213> ORGANISM: Artificial Sequence
<220> FEATURE:
```

```
-continued

<223> OTHER INFORMATION: AC-133 forward primer 2

<400> SEQUENCE: 9
gagaacaata ataggatatt ttgaacatta tctg                             34

<210> SEQ ID NO 10
<211> LENGTH: 27
<212> TYPE: DNA
<213> ORGANISM: Artificial Sequence
<220> FEATURE:
<223> OTHER INFORMATION: AC-133 reverse primer 2

<400> SEQUENCE: 10
gcttgtcata acaggattgt gaatacc                                     27
```

SECONDARY SPROUTING FOR ISOLATION AND EXPANSION OF ENDOTHELIAL SPROUT CELLS AND ENDOTHELIAL PRECURSOR CELLS FROM A MIXED POPULATION AND FOR SCREENING SUBSTANCES

The U.S. Government has a paid-up license in this invention and the right in limited circumstances to require the patent owner to license on reasonable terms as provided for by the terms of Grant NIH 1R03 EY 13841, awarded by the National Eye Institute of the National Institutes of Health.

BACKGROUND OF THE INVENTION

1. Field of the Invention

This invention relates to the medical arts. In particular, it relates to an in vitro method of isolating and expanding a cellular population enriched for cells having one or more physiological and/or immunological features of endothelial precursor cells (EPCs) and uses for those EPCs.

2. Discussion of the Related Art

Angiogenesis is a highly regulated biological process of sprouting new blood vessels from preexisting blood vessels, which supports growth and maturation. Angiogenesis begins in the mammalian embryo when primitive blood vessels are formed from endothelial cell precursors (EPCs; also known as endothelial progenitor cells or endothelial stem cells). Increasingly complex networks of vessels are formed from these primitive precursors.

Endothelial cell precursors progress through various stages before becoming mature cells. The earlier precursor cells are able to give rise to more cell types if given the right signals and environment. Cells derived from older and more mature precursors have a more limited repertoire.

Generally, molecular markers are used to keep track of the different developmental steps taken of endthelial cells, as certain molecules are present only during certain periods. Cells that can give rise to endothelial cells as well as other cell types are called hematopoietic stem/progenitor cells (HSPC) and/or hemangioblasts. The most primitive are usually derived from umbilical cord blood, peripheral blood or bone marrow and are generally positive for CD34 while being negative for CD38 and HLA-DR. CD34$^+$ cells can be further subdivided according to their expression of CD45RA and CD71. Cells which are CD34$^+$ CD45RA$^-$ and CD71$^-$ give rise to multipotent progenitor cells, including those which will produce endothelial cell precursors (angioblasts); those that are CD34$^+$ CD45RA$^+$ and CD71$^-$, give rise to granulocyte and monocye progenitors whereas those which are CD34$^+$ CD45RA$^-$ and CD71$^+$ give rise to erythrocyte progenitors. (Mayani H and Lansdorp P M, *Biology of Human Umbilical Cord Blood-Derived Hematopoietic Stem/Progenitor Cells*. Stem Cells. 1998; 16:153–165).

CD34$^+$ cells can be manipulated by the right culture conditions to produce mature endothelial cells expressing von Willebrand factor, CD31, CD54 and CD62. (Mayani H and Lansdorp P M, *Biology of Human Umbilical Cord Blood-Derived Hematopoietic Stem/Progenitor Cells*. Stem Cells. 1998; 16:153–165). Considerable controversy exists regarding the specific pathway(s), as well as the number of intermediates in the transition between hemangioblasts and differentiated endothelial cells. However, "presumptive hemangioblasts" express CD34, FLK-1, SCL, LMO2 and GATA-2. (Orkin S H and Zon L I. *Hematopoiesis and stem cells: plasticity versus developmental heterogeneity*. Nature Immunology. 2002. 3(4):323–328).

Even though there is strong support for the expression of CD34 in hematopoietic stem cells, many groups have reported it to be "reversible", "changing", or "absent". (Ishikawa F. *Reversible expression of CD34 by hematopoietic stem cells*. Ronsho Ketsueki. 2002. 43(1):1–4; Ogawa M. *Changing phenotypes of hematopoietic stem cells*. Exp Hematol. 2002. 30(1):3–6; Huss R. *Perspectives on the morphology and biology of CD34-negative stem cells*. J Hematother Stem Cell Res. 2000. 9:783–793). These controversies may be due to the different origins of these stem cells (organs vs. blood or bone marrow) or to the analysis of a vast number of potential intermediates in the differentiation pathway.

There is a specific set of markers present only in EPCs, but not in differentiated endothelial cells. These include AC133, CD166, and AML-1. (Asahara T., et al. *Isolation of putative progenitor endothelial cells for angiogenesis*. Science. 1997. 275:964–967; Matsumoto K., et al. *In vitro proliferation potential of AC133 positive cells in peripheral blood*. Stem Cells. 2000. 18:196–203; Ohneda O., et al. *ALCAM (CD166): its role in hematopoietic and endothelial development*. Blood. 2001. 98(7): 2134–2142; Okuda T., et al. *RUNX1/AML-1: a central player in hematopoiesis*. Int. J. Hematol. 2001. 74:252–257).

In contrast, some markers are expressed only on "mature endothelial cells", and not the EPCs, such as CD31, CD36 and CD62, V-Cadherin. (Reyes M., et al. *Origin of endothelial progenitors in human postnatal bone marrow*. J Clin Invest. 2002. 109(3):337–346).

When precursor cells divide, they can either produce daughter cells more mature than themselves (proliferation) or produce more precursor cells like themselves (expansion). The cellular environment, including cytokines and growth factors, controls these processes. (Mayani H and Lansdorp P M, *Biology of Human Umbilical Cord Blood-Derived Hematopoietic Stem/Progenitor Cells*. Stem Cells. 1998; 16:153–165).

In adults, nonpathogenic angiogenesis is restricted and transient, for example, as part of the wound healing process and during the female reproductive cycle in the endometrium and ovarian follicle.

Because of the role angiogenesis is thought to play in human diseases, pathogenic angiogenesis has been intensively studied. The highly regulated process of angiogenesis is considered a physiological response to the balance between the actions of proangiogenic and antiangiogenic factors, synthesized by endothelial cells, stromal cells, blood, the extracellular matrix, and tumor cells (Carmeliet, P. and Jain, R. K., *Angiogenesis in cancer and other diseases*, Nature (2000) 407:249–257 [2000]). When proangiogenic factors are synthesized, stimulated by metabolic stress, mechanical stress, inflammation, or genetic mutations, new blood vessels are created from preexisting ones and pathogenic states result (Carmeliet, P. and Jain, R. K. [2000]). Proangiogenic factors create new blood vessels in six distinct steps: vascular destabilization caused by pericyte detachment, extracellular matrix degradation by endothelial proteases, endothelial cell migration, endothelial cell proliferation, tube formation by endothelial cells, and recruitment of pericytes to stabilize vasculature. (Sato, Y., *Molecular mechanism of angiogenesis. Transcription factors and their therapeutic relevance*, Pharm & Ther 87:51–60 [2000]).

All of these steps are mediated by proangiogenic factors acting in concert with one another. For example, vascular endothelial growth factor (VEGF) and related molecules stimulate vessel leakage, matrix metalloproteases (MMPs) remodel extracellular matrix and release and activate growth factors, platelet-derived growth factor BB (PDGF-BB) and receptors recruit smooth muscle cells, vascular endothelial growth factor receptor (VEGFR) and NRP-1 integrate angiogenic and survival signals, plasminogen activator inhibitor-1 (PAI-1) stabilizes nascent vessels, and angiopoietin 1 (Ang1) and its receptor precursor (Tie2) in turn stabilize vessels (Carmeliet, P. and Jain, R. K. [2000]) 407:249–257).

For many years, tube formation on a reconstituted basement membrane matrix (MATRIGEL™ biological cell culture substrate) has been the assay of choice for the assessment of angiogenesis in vitro (Baatout S., *Endothelial differentiation using Matrigel (review)*, Anticancer Res. 17: 451–6 [1997]; Benelli, R. and Albini, A., *In vitro models of angiogenesis: the use of Matrigel*, Int. J. Biol. Markers. 14, 243–6 [1999]). MATRIGEL™ biological cell culture substrate is derived from the extracellular matrix deposited by a mouse EHS tumor. MATRIGEL™ biological cell culture substrate is a complex mixture of basement membrane proteins (laminin, type IV collagen, entactin/nidogen, and heparan sulfate proteoglycans) and it also contains certain growth factors. (Kleinman, H. K. et al., *Isolation and characterization of type IV procollagen, laminin, and heparan sulfate proteoglycan from the EHS sarcoma*, Biochemistry. 21: 6188–93 [1982]; Vukicevic, S. et al., *Identification of multiple active growth factors in basement membrane Matrigel suggests caution in interpretation of cellular activity related to extracellular matrix components*, Exp Cell Res. 202: 1–8 [1992]). Unlike the commonly used type I collagen gels (Schor, A. M. et al., *Collagen gel assay for angiogenesis*. In: *Methods in molecular medicine, angiogenesis protocols* [Murray J. C., ed.], Humana Press, Totowa, N.J., pp. 145–62 [2001]), the reconstituted basement membrane matrix contains natural substrates that endothelial cells encounter under physiological conditions, i.e., basement membrane components. It has previously been thought that endothelial cells plated on a reconstituted basement membrane matrix 1) stop proliferating, 2) migrate and form capillary-like tubes by 24–36 hr, 3) do not invade the matrix, 4) collapse into clumps, and 5) die. (E.g., Pollman et al., *Endothelial cell apoptosis in capillary network remodeling.*, J. Cell Physiol. 178, 359–70 [1999]; Benelli and Albini [1999]). Because this was thought to be the endpoint of the assay, no previous experiments have extended beyond this point.

The survival of tumors is now considered to be dependent upon tumor angiogenesis. For this reason, cancer chemotherapy is beginning to exploit angiogenesis inhibition as a mechanism to limit tumor metastases and angiogenesis is increasingly being used as a diagnostic/prognostic marker. For example, tumor vascularity in solid tumors may inversely correlate with prognosis, and both basic fibroblast growth factor (bFGF; or FGF-2) and VEGF expression have been reported to predict prognosis. (Takahashi, Y. et al., *Expression of vascular endothelial growth factor and its receptor, KDR, correlates with vascularity, metastasis, and proliferation of human colon cancer*, Cancer Res 55:3964–68 [1995]). Breast cancer prognosis can also be based on the extent of angiogenesis. (Weidner, N. et al., *Tumor angiogenesis: a new significant and independent prognostic factor in early-stage breast carcinoma*, J. Natl. Cancer Inst. 84:1875–1887 [1992]; Horak, E. R. et al., *Angiogenesis, assessed by platelet/endothelial cell adhesion molecule antibodies, as indicator of node metasteses and survival in breast cancer*, Lancet 340:1120–1124 [1992]). Not only are tumor growth, progression, and metastasis dependent on access to vasculature, but it is also apparent that an "angiogenic switch" is activated during the transition from mid to late dysplasia, causing a change in tissue angiogenic phenotype preceding the histological tissue transition. (Hanahan, D. and Folkman, J., *Patterns and emerging mechanisms of the angiogenic switch during tumorigenesis*. Cell. 86:353–64 [1996]).

During tumor-associated angiogenesis, sustained production of angiogenic factors by cancer cells, or indirect macrophage stimulation, causes dysregulated immature vessel growth. (Folkman, J. and Shing, Y., *Angiogenesis*, J Biol. Chem. 267:10931–10934[1992]). Several cytokines and growth factors are highly associated with intratumoral angiogenesis, including bFGF and VEGF which modulate angiogenesis in vivo with a paracrine mode of action. (Bikfalvi, A. et al., *Biological roles of fibroblast growth factor-2*, Endocr. Rev. 18:26–45 [1997]; Ferrara, N. and Davis-Smyth, T., *The biology of vascular endothelial growth factor*, Endocr Rev 18:4–25 [1997]; Relf, M et al., *Expression of the angiogenic factors vascular endothelial cell growth factor, acidic and basic fibroblast growth factor, tumor growth factor-1, platelet-derived endothelial cell growth factor, placenta growth factor, and pleiotrophin in human primary breast cancer and its relation to angiogenesis*, Cancer Res. 57(5):963–69 [1997]; Linderholm, B. et al., *Vascular endothelial growth factor is of high prognostic value in node-negative breast carcinoma*, J. Clin. Oncol. 16:3121–28 [1998]). bFGF and VEGF may synergistically influence angiogenesis, with bFGF modulating endothelial expression of VEGF through both autocrine and paracrine actions. (Seghezzi, G. et al., *Fibroblast growth factor-2 (FGF-2) induces vascular endothelial growth factor (VEGF) expression in the endothelial cells of forming capillaries: An autocrine mechanism contributing to angiogenesis*, J. Cell. Biol. 141(7):1659–73 [1998]).

For these reasons, drugs acting through an antiangiogenic mechanism are contemplated to prevent neoplastic growth. As an example, Hunter et al. described a method of treating a tumor excision site with a composition including paclitaxel or a paclitaxel analog with a polymer to prevent residual blood vessel formation. (U.S. Pat. No. 5,886,026).

In addition to cancer, other pathological states require angiogenesis including diabetes mellitus, Alzheimer's disease, asthma, and hypertension. The pathological progression in endometriosis is also thought to involve angiogensis. (E.g., Taylor, R N et al., *Angiogenic factors in endometriosis*, Ann N Y Acad Sci 955:89–100 [2002]; Shawki, O et al., *Apoptosis and angiogenesis in endometriosis: relationship to development and progression*, Fertil Steril. 77 Suppl 1:S44 [2002]; Gazvani, R et al., *Peritoneal environment, cytokines and angiogenesis in the pathophysiology of endometriosis*, Reproduction 123(2):217–26 [2002]; Taylor, R N et al., *Endocrine and paracrine regulation of endometrial angiogenesis*, Ann N Y Acad. Sci. 943:109–21 [2001]; Gazvani, R et al., *New considerations for the pathogenesis of endometriosis*, Int J Gynaecol Obstet. 2002 Feb.;76(2): 117–26 [2002]; Fujimoto, J et al., *Angiogenesis in endometriosis and angiogenic factors*, Gynecol Obstet Invest. 48 Suppl 1:14–20 [1999]; Healy, D L et al., *Angiogenesis: a new theory for endometriosis*, Hum. Reprod. Update. 1998 Sep.–Oct.;4(5):736–40 [1998]; Matsuzaki, S et al., *Angiogenesis in endometriosis*, Gynecol. Obstet. Invest. 46(2):111–15 [1998]).

Inflammatory disorders can involve excessive angiogenesis in various organs. Blood cells including platelets, mast cells, monocytes, and macrophages release angiogenic factors, such as VEGF, ANG1, bFGF, TGF-β1, PDGF, TNF-α, hepatocyte growth factor (HGF), and insulin-like growth factor (IGF-I). Additionally, blood cells contain proteases that degrade barriers for migrating vasculature and activate growth factors from extracellular matrix. Wound repair is an example of how the inflammatory response influences angiogenesis in a non-pathogenic way. Angiogenesis in wound repair can be described in the following steps: 1) endothelial cells are released from the basement membrane degraded by metalloproteinases and other proteases, and 2) the endothelial cells migrate to connective tissue and differentiate into tubes where they resynthesize the basement membrane, all in response to the proangiogenic factors being secreted at the wound site. (Kleinman, H. K. and Malinda K. M., *Role of angiogenesis in wound healing*, in *Angiogenesis Inhibitors and Stimulators: Potential Therapeutic Implications*, Ed. Mousa, S. A., pp. 102–109 [2000]).

The primary cause of pathological angiogenesis in non-neoplastic disease states is hypoxia. Hypoxia-induced transcription factors (HIFs) induce the expression of angiogenic factors including VEGF, nitric oxide synthase, PDGF, Ang2, and others (Carmeliet, P. and Jain, R. K. [2000]). As a result, hypoxia-induced angiogenesis leads to blindness in premature newborns, diabetics, and hemorrhagic rupture of atherosclerotic plaques. Additionally, vascular remodeling caused by hypoxia induces chronic obstructive lung disease, characterized by the thickening of vascular muscular coat and pulmonary hypertension. Although hypoxia-induced angiogenesis can be pathological, it also salvages ischemic myocardium and promotes survival after stroke. For these reasons, the use of proangiogenic factors has been proposed as therapy for ischemic diseases, such as arteriosclerotic occlusion of the lower limb or angina pectoris/myocardial infarction.

Diabetic retinopathy, the most severe ocular complication of diabetes mellitus, may be defined as a disease of retinal microvasculature. Diabetic retinopathy is the leading cause of new blindness in persons 25 to 74 years of age in the United States, accounting for about 8,000 new blindness cases each year. (Aiello L P et al., *Diabetic retinopathy*, Diabetes Care 21:143–156 [1998]; Lim J I et al., *Review of diabetic retinopathy*, Curr. Opin. Ophthalmol. 2:315–323 [1991]). Two types of diabetic retinopathy are recognized clinically: (1) nonproliferative diabetic retinopathy (NPDR), associated with retinal ischemia, pericyte loss, capillary closure, retinal infarctions/cotton wool spots, retinal hemorrhages, microaneurisms, intraretinal microvascular abnormalities, and macular edema; and (2) proliferative diabetic retinopathy (PDR), associated with intravitreal hemorrhages, optic disc or peripheral neovascularization, preretinal fibrovascular membranes, and vitreoretinal traction with retinal detachments (Aiello L P et al. [1998]; Lim J I et al. [1991]). Sadly, 43% of juvenile-onset and 60% of adult-onset diabetics lose vision within 5 years of the onset of PDR.

Supporting the conclusion that diabetic retinopathy is a disease of retinal microvasculature, abnormally high concentrations of angiogenic growth factors have been detected in the vitreous of diabetic retinopathy and PDR patients. (Aiello L P, and Hata Y., *Molecular mechanisms of growth factor action in diabetic retinopathy*, Curr. Opin. Endocrinol. Diabetes 6:146–156 [1999]; Boulton, M. et al., *Intravitreal growth factors in proliferative diabetic retinopathy: correlation with neovascular activity and glycaemic management*, Br. J. Ophthalmol. 81:228–233 [1997]; Freyberger, H. et al., *Increased levels of platelet-derived growth factor in vitreous fluid of patients with proliferative diabetic retinopathy*, Exp. Clin. Endocrinol. Diabetes 108:106–109 [2000]). Additionally, VEGF induced by hypoxia and hyperglycemia has been implicated in causing PDR neovascularization and vascular hyperpermeability. (Aiello L P, and Hata Y., *Molecular mechanisms of growth factor action in diabetic retinopathy*, Curr. Opin. Endocrinol. Diabetes 6:146–156 [1999]; Aiello, L P and Wong, J S, *Role of vascular endothelial growth factor in diabetic vascular complications*, Kidney Int. 58 (Suppl. 77):113–119 [2000]).

Retinas in proliferative diabetic retinopathy (PDR) have increased expression of VEGF, PlGF, and tenascin, a vascular basement membrane protein. (E.g., Ljubimov A V et al., *Basement membrane abnormalities in human eyes with diabetic retinopathy*, J. Histochem. Cytochem. 1996;44: 1469–1479 [1996]; Spirin K S et al., *Basement membrane and growth factor gene expression in normal and diabetic human retinas*, Curr. Eye Res. 18:490–499 [1999]). Hypoxia-inducible VEGF is considered as the main growth factor that mediates PDR neovascularization (Smith L E et al., *Regulation of vascular endothelial growth factor-dependent retinal neovascularization by insulin-like growth factor-1 receptor*, Nat. Med. 5:1390–1395 [1999]).

However, VEGF inhibitors only partially prevent ocular neovascularization and vessel hyperpermeability. (Campochiaro, P A, *Retinal and choroidal neovascularization*, J. Cell Physiol. 184:301–310 [2000]; Aiello L P, *Vascular endothelial growth factor. 20th-century mechanisms, 21st-century therapies*. Invest. Ophthalmol. Vis. Sci. 38:1647–1652 [1997]; Ozaki H et al., *Blockade of vascular endothelial cell growth factor receptor signaling is sufficient to completely prevent retinal neovascularization*, Am. J. Pathol. 156:697–707 [2000]; Aiello L P, *Vascular endothelial growth factor and the eye: Biochemical mechanisms of action and implications for novel therapies*, Ophthalmic Res. 1997;29:354–362; Aiello L P et al., *Vascular endothelial growth factor-induced retinal permeability is mediated by protein kinase C in vivo and suppressed by an orally effective β-isoform-selective inhibitor*, Diabetes 46:1473–1480 [1997]; Campochiaro P A, *Retinal and choroidal neovascularization*, J. Cell Physiol. 184:301–310 [2000]; Penn J S, Bullard L E, *VEGF signal transduction proteins ERK-1 and ERK-2 are targets for the inhibition of retinal angiogenesis*, Exp. Eye Res. (ICER Abstracts) 71(Suppl. 1):S.5 [2000]).

This implies that other factors may be involved in this process. (See, Castellon, R. et al., *Effects of Angiogenic Growth Factor Combinations on Retinal Endothelial Cells*, Exp. Eye Res. 74:523–35 [2002]). Growth factor synergies have been reported in other tissues. (Goto F et al., *Synergistic effects of vascular endothelial growth factor and basic fibroblast growth factor on the proliferation and cord formation of bovine capillary endothelial cells within collagen gels*, Lab. Invest. 69:508–517 [1993]; Stavri G T et al., *Hypoxia and platelet-derived growth factor-BB synergistically upregulate the expression of vascular endothelial growth factor in vascular smooth muscle cells*, FEBS Lett. 358:311–315 [1995a]; Stavri G T et al., *Basic fibroblast growth factor upregulates the expression of vascular endothelial growth factor in vascular smooth muscle cells. Synergistic interaction with hypoxia*, Circulation 92:11–14 [1995b]; Hata Y et al., *Basic fibroblast growth factor induces expression of VEGF receptor KDR through a protein kinase C and p44/p42 mitogen-activated protein kinase-dependent pathway*, Diabetes 48:1145–1155 [1999]; Miele C et al., *Insulin and insulin-like growth factor-I induce vascular endothelial growth factor mRNA expression via different signaling pathways*, J. Biol. Chem. 275:21695–21702 [2000]).

There remains a need for an in vitro method of isolating and expanding a cellular population enriched for endothelial precursor cells that can be used to further the study of biochemical mechanisms of angiogenesis and antiangiogenesis, and can be employed to screen substances for potential new proangiogenic and antiangiogenic agents that could be useful for therapeutic purposes. These and other benefits are provided by the present invention as described herein.

SUMMARY OF INVENTION

The present invention relates to an in vitro method of isolating and expanding a cellular population enriched for endothelial sprout cells, from a mixed population of mammalian cells originating from a tissue sample. In some embodiments, the inventive method relates to isolating and or expanding a cellular population enriched for cells having one or more physiological and/or immunological features of endothelial precursor cells, from the mixed population of mammalian cells. The method relies on the novel phenomenon of secondary sprouting.

The method involves the steps of culturing the mixed population of mammalian cells, which includes endothelial cells, on a first basement membrane matrix, such as MATRIGEL™ biological cell culture substrate; allowing tube formation by the endothelial cells to occur on the first basement membrane matrix; and, after tube collapse, selecting, from a first collapsed tube on the first basement membrane matrix, at least one viable first endothelial sprout cell expressing one or more elongated morphological processes. In some embodiments, the cell can be one that expresses one or more physiological and/or immunological features of endothelial precursor cells (EPCs).

The endothelial sprout cells and/or EPCs, obtained by the method can be used to assay pro/anti-angiogenic substances that selectively target EPCs (vs. normal differentiated endothelial cells as encountered in other assays). This is particularly useful, because certain angiogenic growth factors such as PDGF exert different, and often opposite, effects on precursor vs. mature endothelial cells.

Thus the present invention also includes an in vitro method for screening a substance for potential proangiogenic or antiangiogenic activity. The method involves culturing a mixed population of mammalian cells comprising endothelial cells on a basement membrane matrix, in the presence of a potential proangiogenic or antiangiogenic agent. Tube formation by the endothelial cells is allowed to occur on the basement membrane matrix; and, after tube collapse, it is detected whether or not secondary sprouting colonies are formed on the basement membrane matrix; and any secondary sprouting colonies that are formed are compared to a control not exposed to the potential proangiogenic or antiangiogenic agent. If in relation to the control there is enhanced secondary sprouting, e.g.: enhanced amount of secondary sprouting (i.e., greater colony numbers), enhanced colony size, enhanced migration (e.g., rate or distance of movement), enhanced viablity and survival potential, enhanced invasive capability (e.g., colony rise above and/or penetration below the surface of the basement membrane matrix), or enhanced mycogenic potential, this indicates potential proangiogenic activity by the substance. If in relation to the control there is an inhibition of secondary sprouting, e.g.: decreased amount of sprouting (i.e., greater colony numbers), smaller colony size, less migration (e.g., rate or distance of movement), poorer viablity and survival potential, less invasive capability (e.g., colony rise above and/or penetration below the surface of the basement membrane matrix), or less mycogenic potential, this indicates potential antiangiogenic activity by the substance. Once the potential of a substance is identified by the inventive method, then, further research can be done to further purify the active component of the substance (e.g., if the substance is a mixture, not a compound), verify its actual effect in vivo and ascertain its clinical usefulness. Thus, the inventive method of screening a substance is of benefit in finding and developing the next generation of proangiogenic and antiangiogenic pharmaceutical drugs. Thus, the inventive in vitro method facilitates the screening and development of new pharmaceuticals for the treatment of cancer and other diseases, in which inhibiting or enhancing the formation of vasculature is a likely therapeutic target.

These and other advantages and features of the present invention will be described more fully by way of the drawings and in a detailed description of the preferred embodiments which follows. By way of further describing the present invention, the disclosure and drawings of commonly owned U.S. patent application Ser. No. 10/328,646, simultaneously filed on Dec. 23, 2002, and entitled ANTI-ANGIOGENESIS BY INHIBITING PROTEIN KINASE CK2 ACTIVITY, are incorporated herein by reference in their entirety.

Cell migration into the wound was counted using the AAB software. Bars represent mean±SEM of at least 3 individual experiments. *, p values of CK2 inhibitor vs. four GFs.

Figure 4:
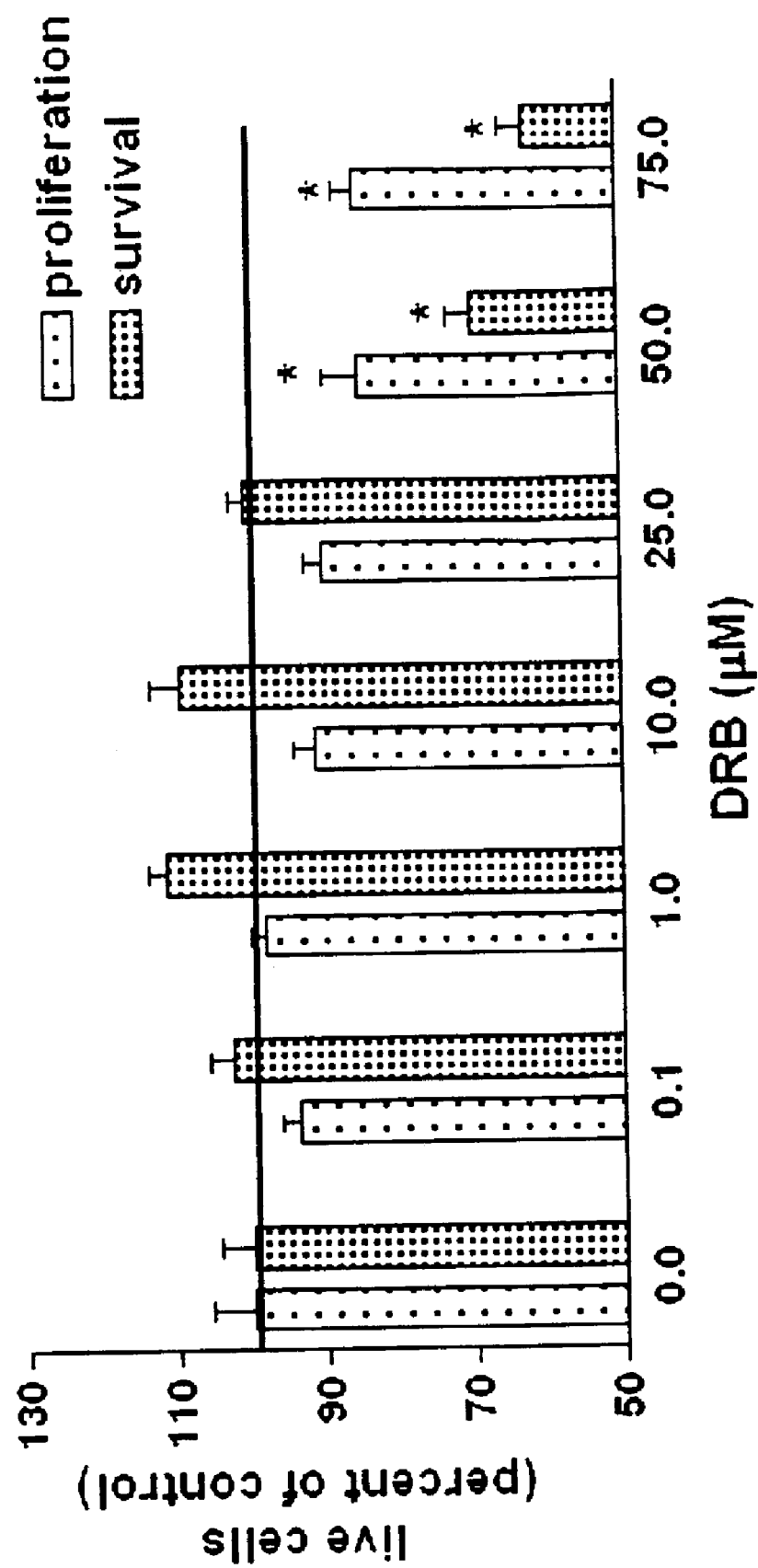

FIG. 4 shows the effect of the CK2 inhibitor DRB on bovine REC proliferation and survival. Cells were plated in medium with 0.5% (survival) or 10% serum (proliferation) containing various concentrations of DRB. The number of live cells was measured on day 6 with MTS assay. Bars represent mean±SDEM of two individual experiments in triplicate. *=p<0.05.

Figure 5:
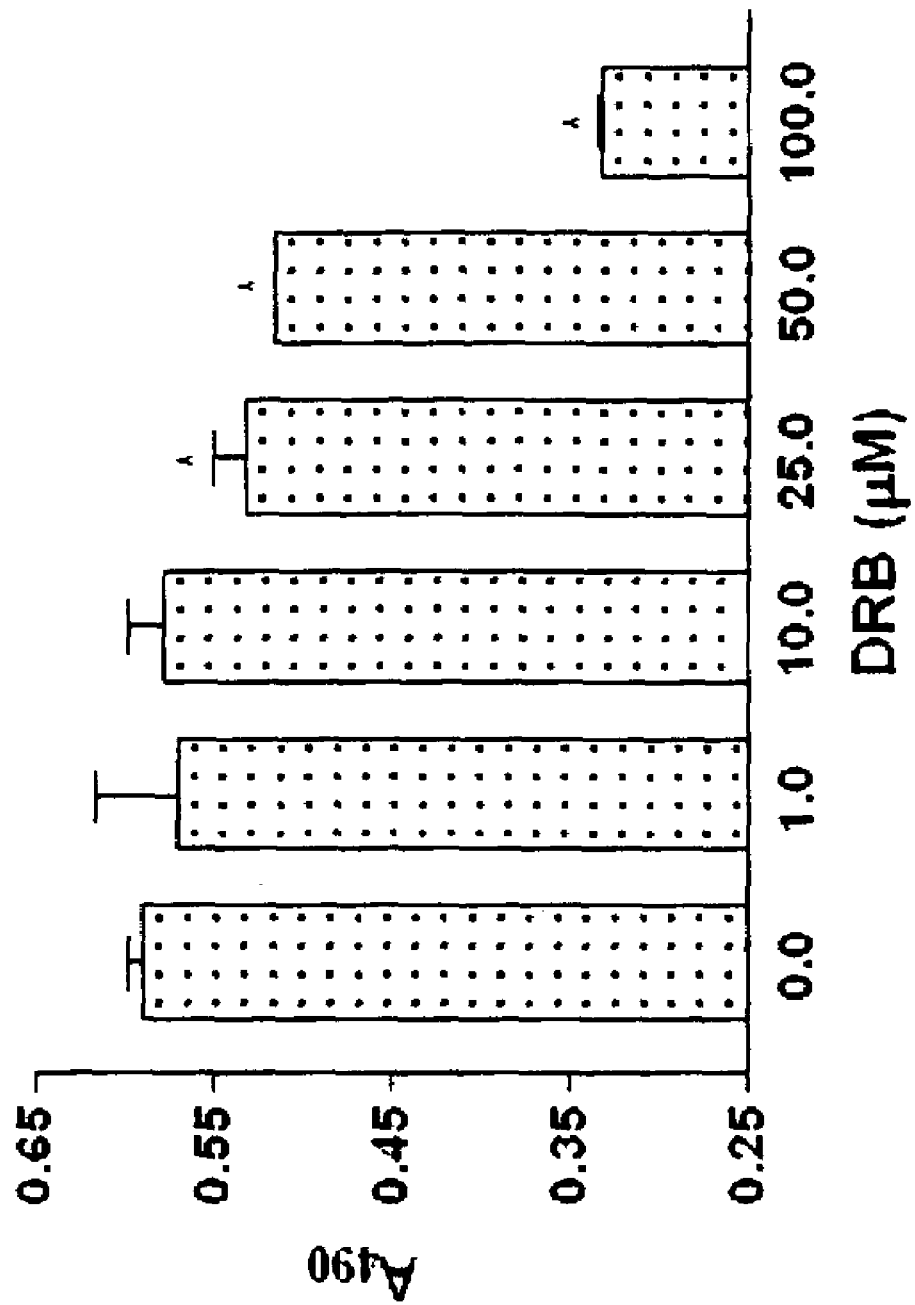

FIG. 5 shows the effect of the CK2 inhibitor DRB on bovine REC secondary sprouting. Cells were seeded on a reconstituted basement membrane matrix (MATRIGEL™ biological cell culture substrate) in medium with 0.5% serum containing various concentrations of DRB. The number of live cells was measured on day 9 with MTS assay. Bars represent mean±SDEM of two individual experiments in duplicate. *=p<0.05.

FIG. 6 shows representative fluorescein angiograms of the retina from a vehicle-treated control mouse (FIG. 6A) and of the retina from an emodin-treated mouse (FIG. 6B). Arrows show neovascular tufts prominent in the vehicle-treated animals.

FIG. 7 shows a quantitation of preretinal neovascularization in untreated, vehicle-treated and emodin-treated mouse retinas.

Figure 8:
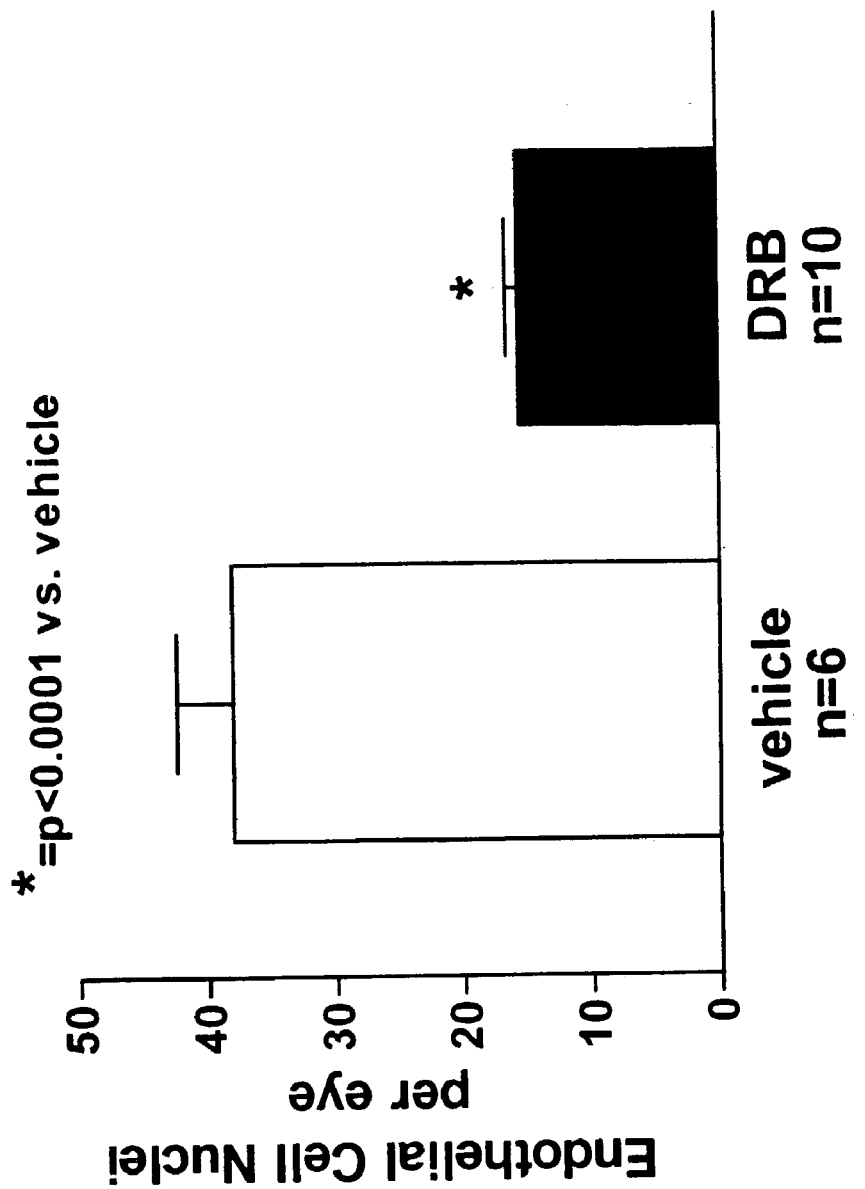

FIG. 8 shows a quantitation of preretinal neovascularization in untreated, vehicle-treated and DRB-treated mouse retinas.

Figure 9:
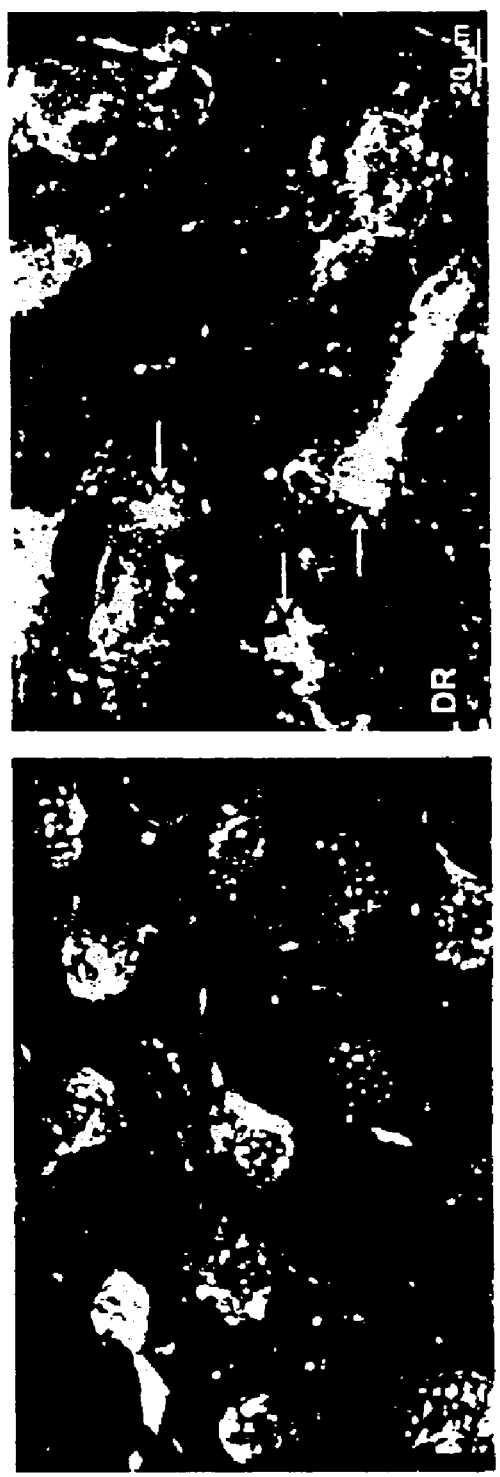

FIG. 9 shows CK2 α subunit expression in cultured REC of normal (N) and diabetic retinopathic (DR) origin as detected by immunohistochemistry. These immunofluorescent pictures were taken with the same exposure time.

Figure 10:
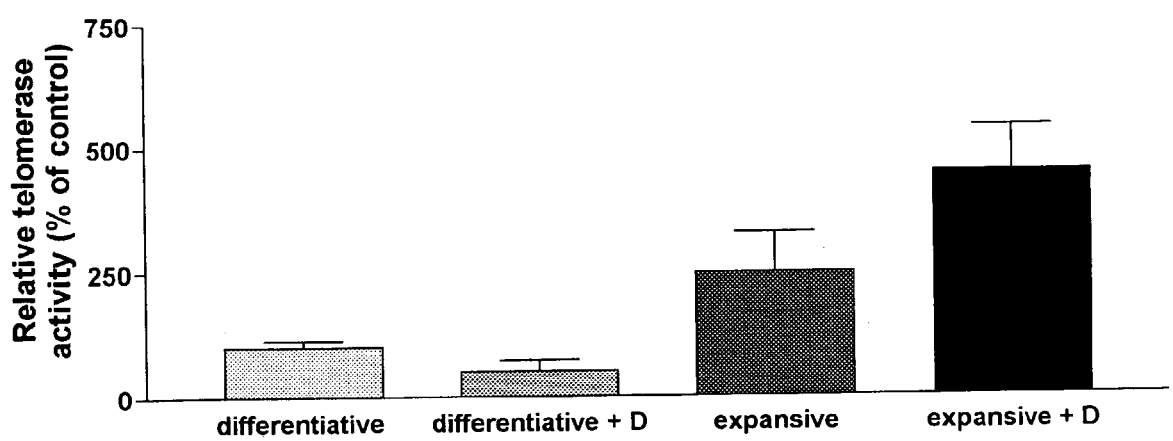

FIG. 10 demonstrates that secondary sprouting colonies grown on BD MATRIGEL™ biological cell culture substrate contain high telomerase activity when compared to the parental cells grown in differentiative medium. PDGF treatment (D) of sprouting colonies under expansive conditions increases the activity of telomerase, indicating a higher proportion of endothelial precursor cells (EPCs) in the treated population, or, possibly, the existence of a more active enzyme in the treated cells. PDGF exerts the opposite effect on differentiated endothelial cells grown under differentiative conditions.

Figure 11:
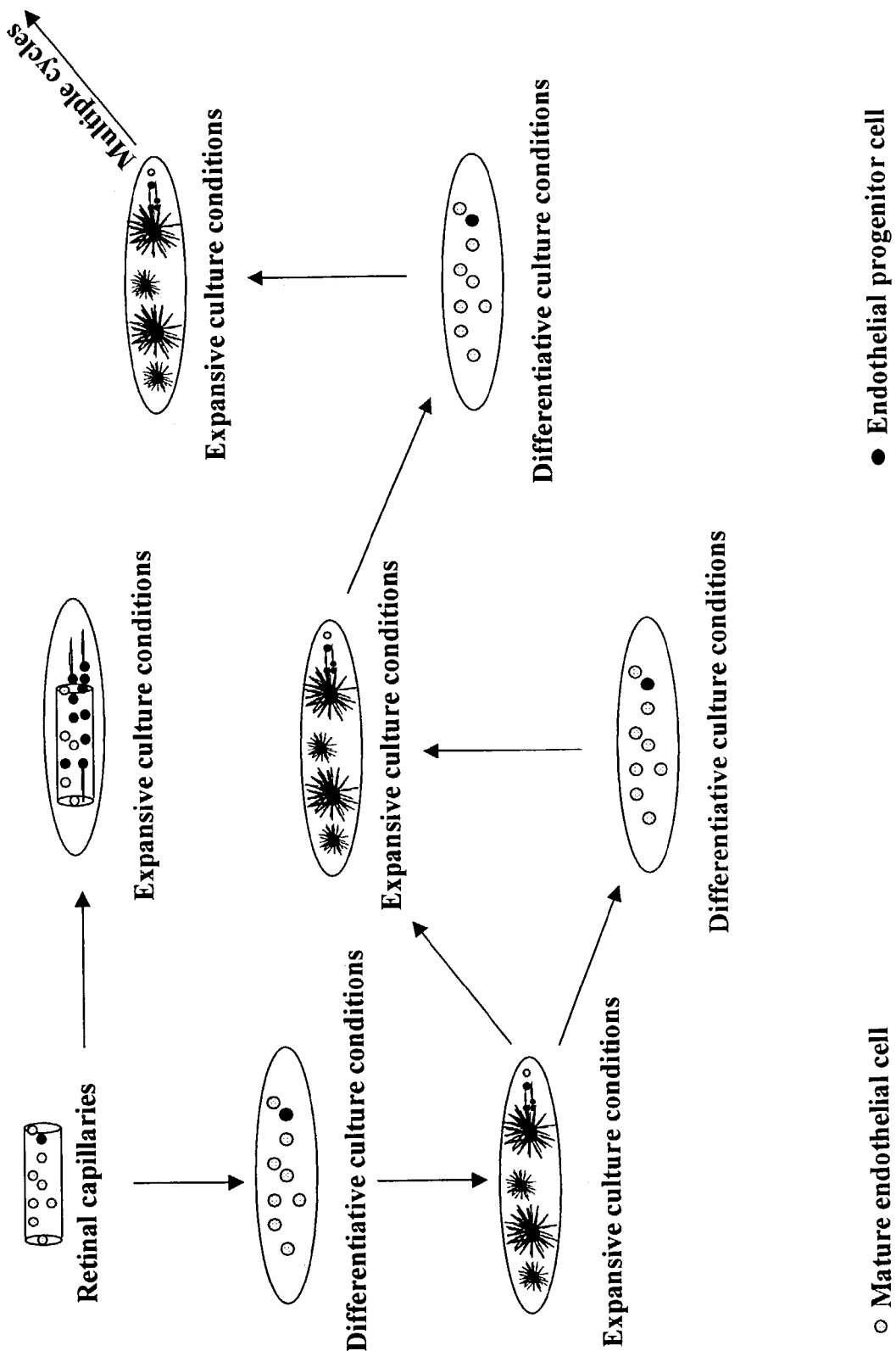

FIG. 11 shows a schematic representation of one embodiment of the inventive method of isolating and expanding a cellular population enriched for cells having one or more physiological and/or immunological features of endothelial precursor cells. As indicated, intact capillaries contain a mixture of EPCs and mature endothelial cells (MECs). After initial plating under differentiative conditions, most cells are MECs, which die under expansive culture conditions. This procedure allows the surviving population of EPCs to proliferate and expand. Further cycles (alternating between differentiative and expansive conditions) enrich the proportion of EPCs in the differentiative cultures but do not significantly enhance the final EPC cell numbers under expansive culture conditions due to space constraints.

Figure 12:
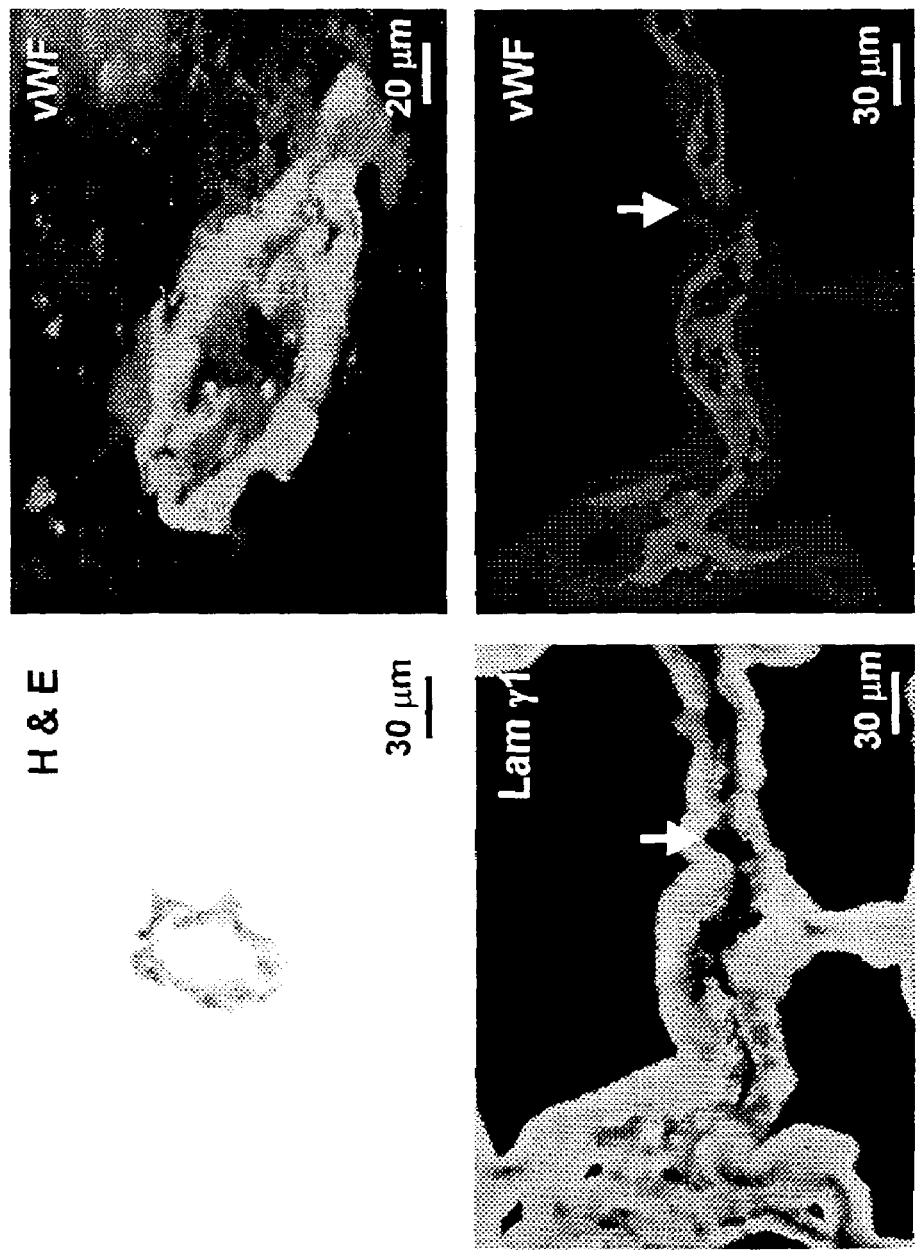

FIG. 12 demonstrates immunohistochemical characterization of secondary sprouting colonies. Sprouting colonies were scooped out of the basement membrne matrix, embedded in OCT and cryosectioned. Sections were stained with hematoxylin and eosin [(H) and (E)] or by indirect immunofluorescence for an endothelial cell marker, von Willebrand factor (vWF), and γ1 chain of laminin (Lam γ1), a major basement membrane component. The top row illustrates the formation of lumenal structures in BREC secondary sprouting colonies. Top left is a cross-section through a tube-like structure with a lumen; top right is a similar structure showing that the tube-forming cells were positive for vWF. The bottom row shows a longitudinal section of a sprouting colony of human REC (double staining of the same section). Cells embedded in the basement membrane matrix were positive for the laminin γ1 chain (bottom left), and were positive for vWF (bottom right). Arrows point to the same location in the double-labeled fluorescence photographs to facilitate orientation.

Figure 13:
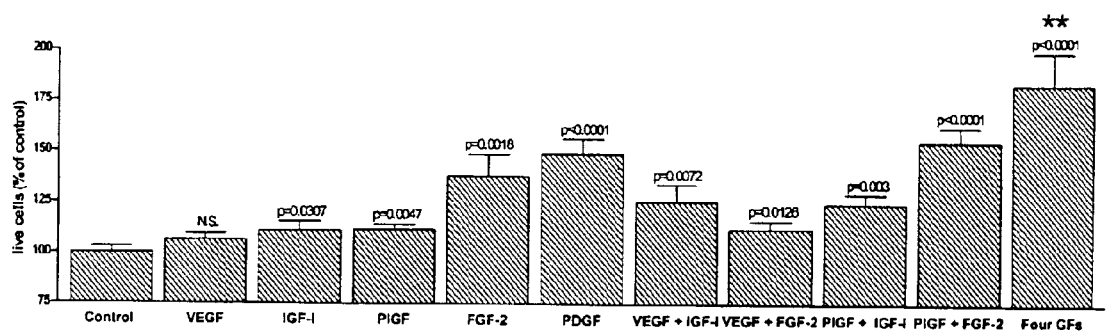

FIG. 13 illustrates enhancement of secondary sprouting by growth factors. BREC were seeded on reconstituted basement membrane matrix and cultured with 0.5% FCS medium containing growth factors (10 ng mL$^{-1}$). Live cells were quantitated on day 7 using the MTS assay. Data represent mean±S.E. (M.) of five experiments in duplicate. P-values have been calculated using Student's t-test vs untreated (control) cultures. **P<0.0001 vs all other columns by one-way ANOVA. N.S.=non-significant. Individual growth factors had slight effects on secondary sprouting, with PDGF-BB being the most potent. However, combinations of two and especially four growth factors (excluding PDGF-BB) markedly enhanced this parameter.

Figure 14A:
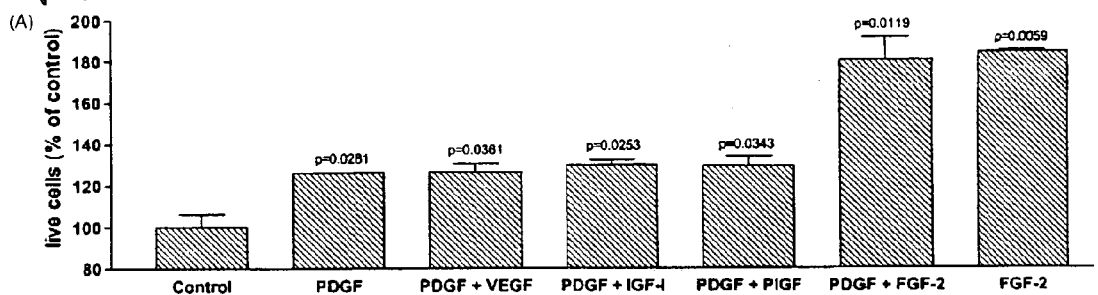
Figure 14B:
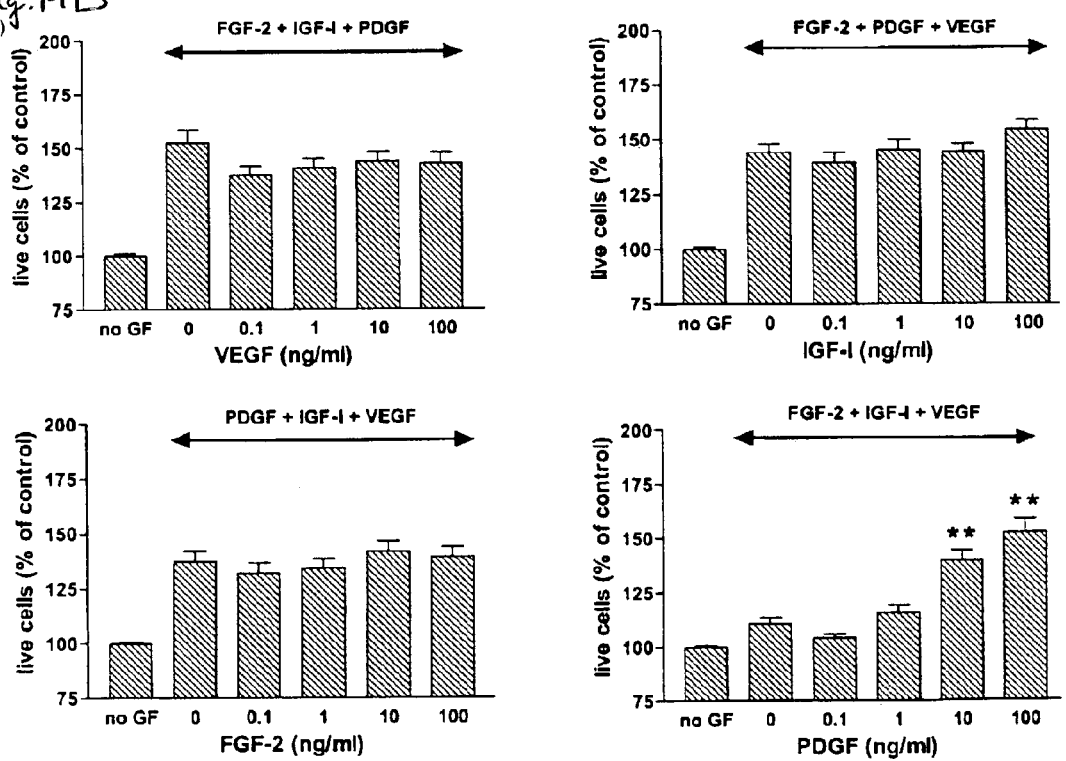

FIG. 14 illustrates the effects of PDGF-BB and growth factor combinations on secondary sprouting. In FIG. 14A, BREC were seeded on reconstituted basement membrane matrix, incubated with 0.5% FCS medium, and tube formation was allowed, followed by collapse. On day 3, FGF-2 or PDGF-BB±VEGF, IGF-I, PlGF or FGF-2 were added (10 ng mL$^{-1}$ final concentration for each growth factor, except PDGF-BB at 1 ng mL$^{-1}$). Cells were cultured for another 5 days and live cells were quantitated using the MTS assay. Data represent mean±S.E. (M.) of two experiments in triplicate. P-values have been calculated using Student's t-testy vs untreated (control) cultures. PDGF-BB effect was not additive with that of individual growth factors. In FIG. 14B, BREC were seeded and cultured as above. On day 3, cells were treated with various combinations of three growth factors, as indicated above the double-headed arrows in FIG. 14B, at a constant concentration (10 ng mL$^{-1}$ each) plus variable concentrations of a fourth factor (0–100 ng mL$^{-1}$). Cells were cultured for another 5 days, and live cells were quantitated using the MTS assay. Data represent mean±S.E. (M.) of five experiments in duplicate. **P<0.05 vs PDGF=0 using the Student's t-test. Only PDGF-BB effect was additive with that of combined growth factors.

DETAILED DESCRIPTION OF THE PREFERRED EMBODIMENTS

The present invention relates to an in vitro method of isolating and expanding a cellular population enriched for cells having one or more physiological and/or immunological features of endothelial precursor cells, from a mixed population of mammalian cells originating from a tissue sample.

Figure 2:
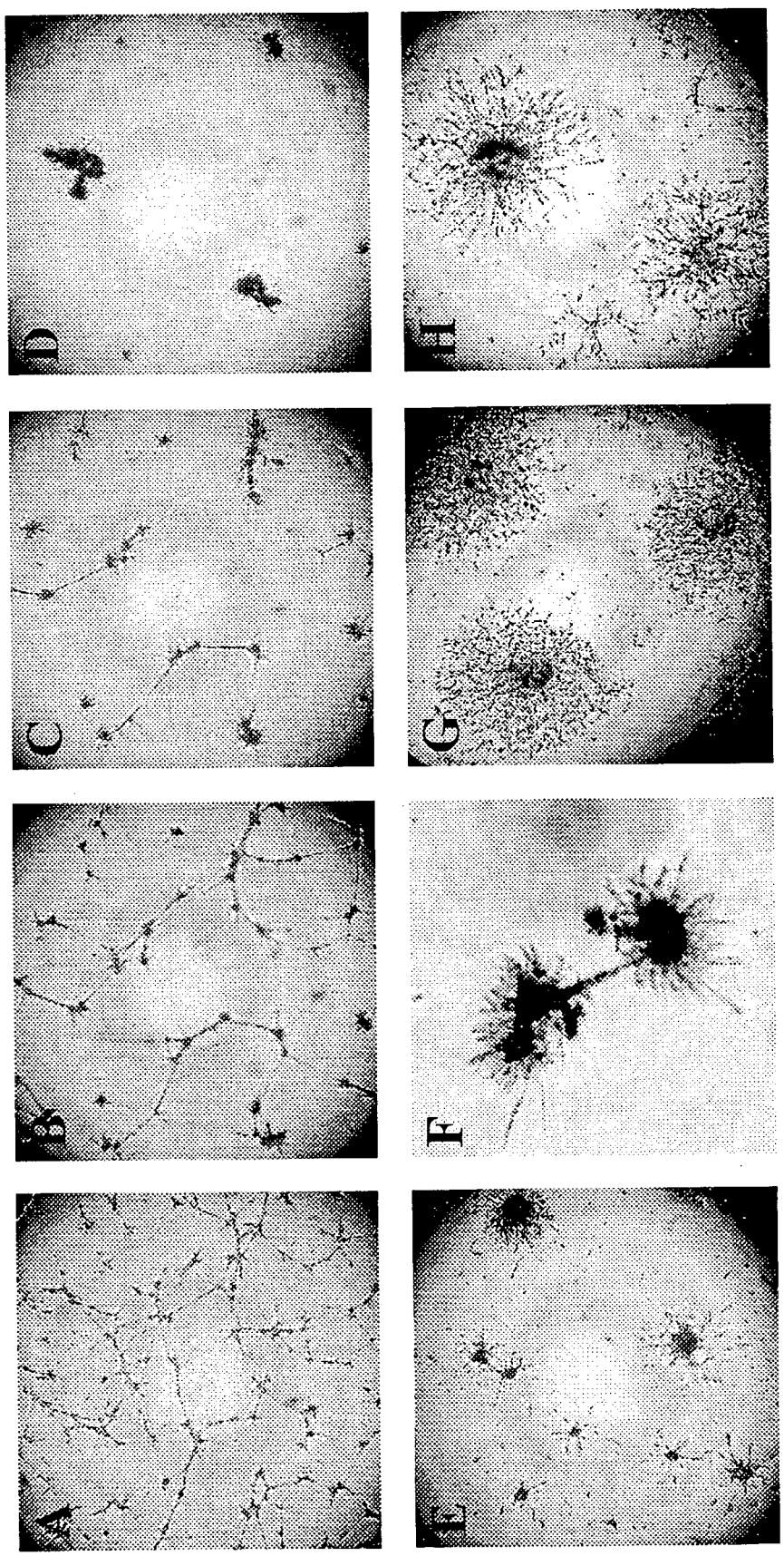
FIG. 2 shows secondary sprouting on BD MATRIGEL™ biological cell culture substrate (a basement membrane matrix). REC form capillary-like tubes (FIG. 2A, FIG. 2B). In 24 hr, tubes start shortening (FIG. 2C), cells aggregate into clumps (FIG. 2D), and reportedly die by apoptosis (i.e., programmed cell death) within 48 hr. (Albini A, *Tumor and endothelial cell invasion of basement membranes. The Matrigel chemoinvasion assay as a tool for dissecting molecular mechanisms*, Pathol. Oncol. Res. 4:230–241 [1998]). Due to a longer examination time, it was unexpectedly observed that the supposedly dead aggregates contained living cells that by day 5 proliferated, migrated and invaded basement membrane matrix (BD MATRIGEL™ biological cell culture substrate) forming three-dimensional spheres (FIG. 2E). In some instances, separate spheres initiated cell—cell contacts resulting in connecting structures resembling larger capillaries (FIG. 2F). This secondary sprouting process was greatly enhanced by the addition of 10 ng/mL PDGF-BB (FIG. 2G) or FGF-2 (FIG. 2H). Pictures were taken in a Leica inverted microscope with a 4× (FIGS. 2A–2E, 2G, and 2H) or a 10× (FIG. 2F) objective. (See, Castellon, R. et al., *Effects of Angiogenic Growth Factor Combinations on Retinal Endothelial Cells*, Exp. Eye Res. 74:523–35 [2002]).
Figure 3:
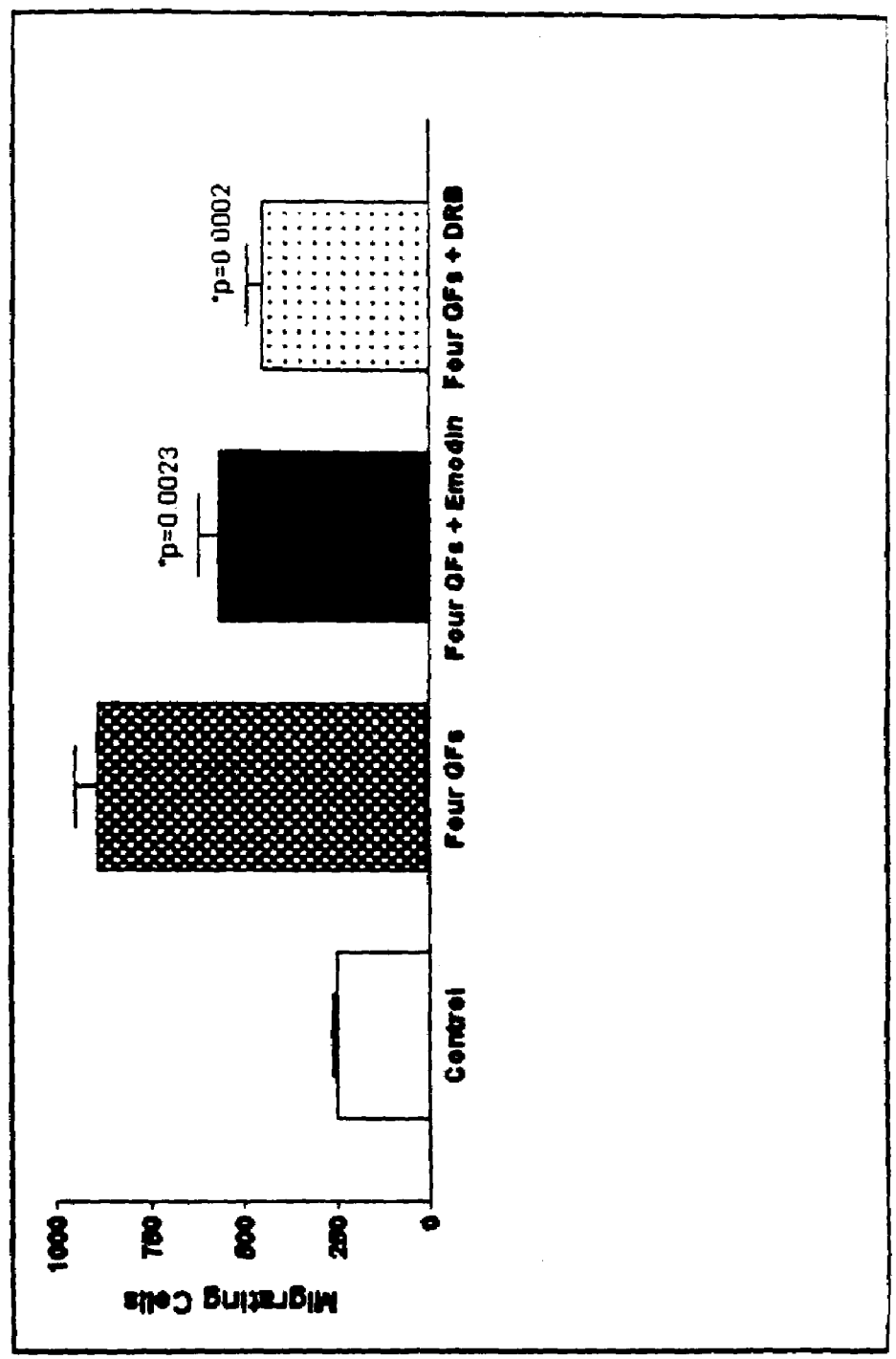
FIG. 3 shows significant inhibitory effect of specific CK2 inhibitors on growth factor (GF)-mediated cell migration. Confluent bovine REC monolayers were wounded and cultured for 7 days in 0.5% serum-containing medium with four growth factors (IGF-1+FGF-2+VEGF+PlGF at 10 ng/ml each)±CK2 inhibitors, emodin (10 μM) or DRB (15 μM).

The method relies on the novel phenomenon of secondary sprouting. "Secondary sprouting" is a process in which endothelial, and endothelial precursor cells, placed on a reconstituted basement membrane matrix are able to survive, proliferate, migrate, and invade the matrix several days after tube collapse. It was previously known that endothelial cells plated on basement membrane matrix stopped proliferating, formed capillary-like hollow tubes for 24–48 hr did not invade the matrix, collapsed into clumps, and died (Benelli R and Albini A, *In vitro models of angiogenesis: the use of Matrigel*, Int. J. Biol. Markers 14:243–246 [1999];

Pollman, M J et al., Endothelial cell apoptosis in capillary network remodeling, J. Cell Physiol. 178:359–70 [1999]). This was heretofore thought to be the endpoint of the assay, since all the cells were presumed to be non-viable. However, as described herein, it was observed that some cells survive following tube collapse. They 1) proliferate, 2) migrate, 3) form spherical colonies that remain alive for weeks, 4) invade basement membrane matrix (e.g., BD MATRIGEL™ biological cell culture substrate or GFR MATRIGEL™ biological cell culture substrate), and 5) can reassemble into larger tubes. Cells from these sprouting colonies, which arise predominantly, but not necessarily (given the migratory capacity of the endothelial sprout cells), in the nodes of intersecting collapsed tubes (to which collapsing tubes tend to retract), and sometimes at other sites in or on the collapsed tubes, are microscopically observed to possess elongated morphological processes about 50 to about 500 micrometers long, i.e., "sprouts", one or two of which extend from a single individual cell. (FIG. 2). One or more of these endothelial sprout cells can be selected in accordance with the present invention.

The extent of secondary sprouting is determined, for example, by detecting, measuring or observing the amount of sprouting (i.e., colony numbers), colony size, cell migration (e.g., rate or distance of movement), cell viablity and survival potential, invasive capability (e.g., colony rise above and/or penetration below the surface of the basement membrane matrix), or mycogenic potential.

As used herein, the term "mammal" or "mammalian" refers to vertebrate animals belonging to the class Mammalia, including all that possess hair and suckle their young, e.g., humans, non-human primates (e.g., monkeys, baboons, apes), rodents (e.g., rats, mice, guinea pigs), lagomorphs (e.g., rabbits), bovine, porcine, ovine, canine, feline, equine, elephant, and the like.

"Endothelium" is a layer of epithelial cells that lines the cavities of the heart, blood vessels, lymph vessels, retina, and the serous cavities of the mammalian body, originating from the mesoderm. Endothelial cells constituting the endothelium can come from either existing endothelium or from bone marrow-derived endothelial precursor cells circulating in the blood.

An "endothelial cell" is a typically thin, flattened cell that is a constituent cell of the endothelium, is part of an endothelial tissue sample, or is a cultured cell originating from an endothelial tissue sample. A vascular endothelial cell is an example. The expressions "differentiated endothelial cell" or "mature endothelial cell" are used herein interchangeably, and denote endothelial cells expressing physiological and/or immunological features of terminally differentiated endothelial cells, including markers, such as CD31, CD36 and CD62, V-Cadherin. (Reyes M., et al. *Origin of endothelial progenitors in human postnatal bone marrow*. J Clin Invest. 2002. 109(3):337–346). Included among endothelial cells are secondary, tertiary, and further cultured cells derived from a primary endothelial cell culture, in vitro, which cells continue to exhibit surface markers known to be characteristic of endothelial cells.

An "endothelial sprout cell" is a cell of endothelial origin expressing one or more elongated morphological processes about 50 to about 500 micrometers long. Endothelial sprout cells typically possess a spindle-shape morphology. They are adept at cell migration and invasion into a basement membrane matrix, such as MATRIGEL™ biological cell culture substrate. Under expansive culture conditions they are highly proliferative and able to survive and remain viable (if not proliferating) for at least about a month on a first basement membrane matrix after tube collapse. Endothelial sprout cells can be CD34[31] or CD34+. Under differentiative culture conditions, the phenotype of an endothelial sprout cell generally reverts to a phenotype indistinguishable from a mature endothelial cell and is capable of reversion back again to the typical endothelial sprout cell phenotype after tube formation and collapse under expansive culture conditions, i.e., secondary sprouting, as further described herein.

An "endothelial precursor cell" (EPC) is a stem cell that can differentiate into a mature endothelial cell in response to certain cytokines. Endothelial precursor cells characteristically express AC133, CD166, AML-1, uPA, tPA, CD31, flk-1, flt-1, tie-2, the capacity to take up acetylated LDL, and the presence of cytoplasmic Weibel-Palade bodies, in contrast to hematopoietic precursor cells that develop from a stem cell lineage in common with endothelial precursor cells. (See, e.g., Choi, K. et al., *A common precursor for hematopoietic and endothelial cells*, Development 125:725–32 [1998]). EPCs characteristicly overexpress telomerase, compared to mature endothelial cells. Morphologically EPCs are polymorphic; they can be flattened, spherical, or can possess a sprout morphology that exhibits one or more morphological processes about 50 to about 500 micrometers long extending from the central mass of the cell. A hallmark characteristic of EPCs, in vitro, is that they can engage in both proliferation (give rise to differentiated daughter cells), under differentiative culture conditions, and in expansion (give rise to more precursors), under expansive culture conditions. These two characteristics are present in secondary sprouting colonies. FIG. 11 shows that secondary sprouting colonies, if taken out of the expansive culture conditions and are cultured under differentiative conditions, engage in proliferation, giving rise to large monolayers of differentiated endothelial cells. A few progenitors remain undifferentiated, however, and are able to survive the next round of MATRIGEL™ biological cell culture substrate culturing and form secondary sprouts again, which can be further subcultured. The secondary sprouting colonies can be taken in and out of their expansive environment successfully and successively for at least five cycles. This is a hallmark of cells isolated and expanded via secondary sprouting in accordance with the present invention, which gives further support to the fact that secondary sprouting cells (i.e., endothelial sprout cells) indeed include a substantial subpopulation of endothelial precursor cells. This sequential in vitro phenomenon, in accordance with the present invention, is analogous to the 'sequential transplantation' assay used in vivo to determine the viability and nature of stem cells. (Nakauchi H., *Isolation and characterization of the hematopoietic stem cell*, Rinsho Ketsueki 1995. 36(5):400–5).

"Expansive culture conditions" are culture conditions that induce cell division and proliferation, which culture conditions include incubation on a basement membrane matrix, such as MATRIGEL™ biological cell culture substrate, in a relatively low serum growth medium (e.g., 50% F-12, 50% low-glucose DMEM with antibiotics/antimycotics and 0.5% fetal calf serum [FCS] without supplements, plus 10 ng/mL PDGF-BB or FGF-2). "Differentiative culture conditions" include incubation on a surface that is not a basement membrane matrix, for example, on a plastic or glass culture plate surface, in a standard cell culture medium, in a growth medium containing either a low or high concentration of serum (e.g., 50% F-12, 50% low-glucose DMEM with antibiotics/antimycotics [Invitrogen] and 0.5–20% FCS, supplemented with insulin/transferrin/selenium [ITS] and endothelial cell growth supplement [ECGS]). (E.g., see, Castellon, R. et al., *Effects of angiogenic growth factor combinations on retinal endothelial cells*, Exp. Eye Res. 74:523–35 [2002]). In some embodiments of the inventive methods, the cell culture medium that is supplied to the mixed population of mammalian cells, under expansive culture conditions, further comprises one or more angiogenic growth factors, such as but not limited to, platelet derived growth factor (PDGF)-BB, fibroblast growth factor (FGF)-2, vascular endothelial growth factor (VEGF), insulin-like growth factor (IGF)-I, and placental growth factor (PlGF).

An antiangiogenic effect or activity is an inhibition of one or more processes involved in angiogenesis, including in vivo, the dissolution of extracellular matrix (e.g., invasion) and the growth and survival of cells forming new blood vessels (e.g., endothelial cells and pericytes), and as detectable in vitro, the inhibition of endothelial cell proliferation, survival, migration, and/or secondary sprouting. A proangiogenic effect or activity is an enhancement of one or more processes involved in angiogenesis, including in vivo, the dissolution of extracellular matrix (e.g., invasion) and the growth and survival of cells forming new blood vessels (e.g., endothelial cells and pericytes), and as detectable in vitro, the inhibition of endothelial cell proliferation, survival, migration, and/or secondary sprouting.

In accordance with the method, the parental culture of mixed cells can be obtained originally from a small tissue sample (biopsy) containing blood vessels from a mammalian subject, such as a human patient, then expanded in culture according to the inventive method and reinfused to reconstitute vasculature in needed areas.

The inventive methods involve culturing a population of mammalian cells comprising endothelial cells on a basement membrane matrix. A "mixed" population of mammalian cells originates from a tissue sample, and includes endothelial cells (e.g., vascular endothelial cells), but can also include other cell types, such as but not limited to, endothelial precursor cells, pericytes, smooth muscle cells, fibroblasts, lymphocytes; and/or other specialized cells particular to a particular tissue, e.g., hepatocytes (liver); enterochromaffin cells (intestines), and the like.

A "tissue" is a group of similar cells united to perform a specific physiologic function. For example, vascular tissue is found throughout the body to carry blood; and blood itself is regarded as a tissue, such that a blood sample is also a tissue sample for purposes of the present invention. The tissue can be organized as an organ, for example, an eye, kidney, liver, heart, brain, esophagus, stomach, intestine, pancreas, breast, ovary, uterus, testis, prostate, spleen, parotid gland, adrenal, submaxillary gland, sublingual gland, lymph node, lung, bone marrow, mediastinum, or skin, or as a subpart of an organ, such as retinal tissue, choroidal tissue, vascular tissue, cervix uteri, or endometrial tissue. In accordance with the invention, the tissue sample is obtained by being collected from a mammalian subject by direct sampling, or by being gathered, received and/or transported for the purpose of practicing the method. Direct sampling of tissue is by any known means, including but not limited to, blood draw or biopsy by any suitable surgical technique, such as laproscopic biopsy, percutaneous biopsy, stereotactic biopsy, tissue swab or scrape, and the like. The tissue sample is alternatively obtained from cultured mammalian cells originating from a primary tissue sample. Tissue samples can optionally be stored by well known storage means that will preserve the cells in a viable condition, such as quick freezing, or a controlled freezing regime, in the presence of a cryoprotectant, for example, dimethyl sulfoxide (DMSO), glycerol, or propanediol-sucrose.

For purposes of the present invention, the basement membrane matrix is a simulated or reconstituted in vitro solid substrate, which at least partially mimics the milieu of extracellular matrix, characteristically found under epithelial cells. In vivo, there are typically two distinct layers: the basal lamina, immediately adjacent to the cells, is a product of the epithelial cells themselves and contains collagen type IV, and the reticular lamina, which is produced by fibroblasts of the underlying connective tissue and contains fibrillar collagen. In vitro, the basement membrane matrix need not be so laminated.

Methods are known for isolating basement membrane proteins and using them to produce a basement membrane matrix suitable for use in the present inventive methods. (E.g., Kleinman et al., *Reconstituted basement membrane complex with biological activity*, U.S. Pat. No. 4,829,000; Reid et al., U.S. Pat. No. 4,642,292; Brocks et al., U.S. Pat. No. 5,147,782; Takehisa et al., JP1124465)

Alternatively, the basement membrane matrix can be obtained commercially and prepared for use according to the manufacturer's instructions. For example, BD MATRIGEL™ biological cell culture substrate Basement Membrane Matrix (BD Biosciences) is a solubilized basement membrane matrix preparation extracted from the Engelbreth-Holm-Swarm (EHS) mouse sarcoma, a tumor rich in extracellular matrix proteins. Its major component is laminin, followed by collagen IV, entactin, and heparan sulfate proteoglycan. It also contains TGF-β fibroblast growth factor, tissue plasminogen activator, and other growth factors which occur naturally in the EHS tumor. At room temperature, BD MATRIGEL™ biological cell culture substrate Matrix polymerizes to produce biologically active matrix material resembling the mammalian cellular basement membrane. A Growth Factor Reduced (GFR) MATRIGEL™ biological cell culture substrate product is also preferred as the basement membrane matrix, as an alternative to BD MATRIGEL™ biological cell culture substrate Matrix, for applications where a more highly defined basement preparation is desired. Phenol red-free basement membrane matrix products are also commercially available for use when assays which require color detection (i.e. fluorescence) are to be performed.

The inventive methods also involve allowing tube formation by the endothelial cells to occur on a first, second, or third (or additional fresh) basement membrane matrix. "Tube formation" is a phenomenon that occurs when endothelial cells are plated on a basement membrane matrix, such as BD MATRIGEL™ biological cell culture substrate; the cells stop proliferating, display high motility and cell—cell communication; within about 24–48 hours the cells align and form a three dimensional network of capillary-like hollow tubes, but do not invade the matrix. After about 48 hours the tubes typically collapse into clumps, and most cells die, but as is shown herein, not all cells die. (Benelli R, Albini A, *In vitro models of angiogenesis: the use of Matrigel*, Int. J. Biol. Markers 14:243–246 [1999]).

It is after this tube collapse that endothelial sprout cells are selected from sprouting colonies in the in vitro method of isolating and expanding, from a mixed population of mammalian cells originating from a tissue sample, a cellular population enriched for cells having one or more physiological and/or immunological features of endothelial precursor cells. Proliferating cells are engaged in a cycle of cell division, which is detected, for example, by an increase in cell number under expansive culture conditions. Even after cell proliferation ceases, the endothelial sprout cells continue to survive, migrate, and invade the basement membrane matrix. The endothelial sprout cell(s) can be selected based on their elongated spindle-like morphology ("sprouts"), which is markedly in contrast to the flattened morphology of endothelial cells. Selecting the cells is done by physically removing with known aseptic cell manipulation techniques a single cell, a plurality of cells, a visible clump of cells from a sprouting colony, or an entire colony. Selection can employ any suitable mechanical means, such as aspiration with a pipet or micropipet, removal with a probe, loop, rod, forceps, microforceps, or other implement.

Selection is preferably done within about 7 to about 14 days after tube collapse, when the cells are at their maximum proliferative capacity, but selection can also be done any time during the period immediately after tube collapse until about one month after tube collapse, after which the cells begin to die.

In one embodiment, the selected endothelial sprout cell(s) express, or contain a subpopulation of cell(s) that express, one or more physiological and/or immunological features of an endothelial precursor cell, such as but not limited to, expression of a marker, such as AC133, CD166, AML-1, uPA, and/or tPA. In another embodiment the one or more physiological and/or immunological features of endothelial precursor cells is, or includes, overexpression of telomerase, compared to normal differentiated endothelial cells, which telomerase oevrexpression can be detected by any suitable immunochemical, molecular (e.g., by mRNA amplification and/or hybridization analysis), or enzymological detection means. (E.g., Armstrong et al., *mTert expression correlates with telomerase activity during the differentiation of murine embryonic stem cells*. Mech Dev. 2000. 97(1–2):109–116; Yang, J., et al., *Stem and germline cells are among the only cells in postnatal tissues that continue to express telomerase activity*, J. Biol. Chem. 274(37):26141–26148 [1999]; Hsiao, R. et al., *Mature endothelial cells express very low levels of telomerase and it's lost during the first five divisions in vitro*, Anticancer Res 17:827–832 [1997]; Kolquist, K A et al., Nature Genet 19:182–186 [1998] as reviewed by Chang E et al., J. Invest. Dermatol. 118:752–8. [2002]).

The expression of the marker by the selected cell(s) can be detected. Detection of marker protein can be by any known immunochemical means, such as, but not limited to, enzyme-linked immunosorbent assay (ELISA), immunofluorescent assay (IFA), immunoelectrophoresis, immunochromatographic assay or immunohistochemical staining, employing anti-marker polyclonal or monoclonal antibodies or antibody fragments, for example Fab, Fab', F(ab')$_2$, or F(v) fragments, that selectively bind a marker protein. (E.g., C.D. Lu et al., *Expression of a novel anti-apoptosis gene, survivin, correlated with tumor cell apoptosis and p53 accumulation in gastric carcinomas*, Cancer Res. 58(9): 1808–12 [1998]; C. Adida et al., *Developmentally regulated expression of the novel cancer anti-apoptosis gene survivin in human and mouse differentiation*, Am. J. Pathol. 152(1): 43–49 [1998]).

Alternatively, detecting the expression of markers by the selected cells is accomplished by any of numerous known methods of amplification of marker-specific nucleic acid segments in the form of RNA or cDNA. Typically, before amplification, it is preferable to extract or separate mRNA from DNA in a sample and to amplify nucleic acids remaining in that fraction of the sample separated from the DNA, to avoid false positives that are caused by amplification of contaminating marker-specific genomic DNA in the original specimen. The amplifications products, if any, are then analyzed to detect the presence of marker gene-specific amplification products. For interpretation of negatives (no marker-specific amplification products) analysis is preferably carried out following a control amplification of nucleic acids specific for a housekeeping gene, for example, a gene encoding β-actin, phosphofructokinase (PFK), glyceraldehyde 3-phosphate dehydrogenase, or phosphoglycerate kinase. Only if expression of the housekeeping gene is detected in the sample, is the absence of marker gene expression reliably accepted.

With increasing sensitivity of amplification and analysis methods employed, it becomes increasingly preferable to determine the expression level of marker gene, e.g., telomorase, relative to expression of a housekeeping gene. The ratio of marker expression to housekeeping gene expression is determined, for example, by real-time PCR methods or densitometric measurement and analysis of electrophoretic bands after amplification. When the ratio of marker expression to housekeeping gene expression exceeds a normal cell standard range and/or approximates an abnormal cell standard range, this indicates overexpression of marker gene product.

mRNAs are amplified by any suitable amplification method. For example, a reverse transcriptase-mediated polymerase chain reaction (RT-PCR) can be employed to amplify marker-specific nucleic acids. Briefly, two enzymes are used in the amplification process, a reverse transcriptase to transcribe marker-specific cDNA from a marker-specific mRNA template in the sample, a thermal resistant DNA polymerase (e.g., Taq polymerase), and marker-specific primers to amplify the cDNA to produce marker-specific amplification products. The use of limited cycle PCR yields semi-quantitative results. (E.g., Gelfand et al., *Reverse transcription with thermostable DNA polymerase-high tempreature reverse transcription*, U.S. Pat. Nos. 5,310,652; 5,322,770; Gelfand et al., *Unconventional nucleotide substitution in temperature selective RT-PCR*, U.S. Pat. No. 5,618,703).

Single enzyme RT-PCR can be employed to amplify marker-specific nucleic acids. Single enzymes now exist to perform both reverse transcription and polymerase functions, in a single reaction. For example, the Perkin Elmer recombinant *Thermus thermophilus* (rTth) enzyme(Roche Molecular), or other similar enzymes, are commercially available.

Alternatively, transcription-mediated amplification (TMA) is employed to amplify marker-specific nucleic acids. (E.g., K. Kamisango et al., *Quantitative detection of hepatitis B virus by transcription-mediated amplification and hybridization protection assay*, J. Clin. Microbiol. 37(2):310–14 [1999]; M. Hirose et al., *New method to measure telomerase activity by transcription-mediated amplification and hybridization protection assay*, Clin. Chem. 44(12)2446–52 [1998]). Rather than employing RT-PCR for the amplification of a cDNA, TMA uses a probe that recognizes a marker-specific (target sequence) RNA; in subsequent steps, from a promoter sequence built into the probe, an RNA polymerase repetitively transcribes a cDNA intermediate, in effect amplifying the original RNA transcripts and any new copies created, for a level of sensitivity approaching that of RT-PCR. The reaction takes place isothermally (one temperature), rather than cycling through different temperatures as in PCR.

Other useful amplification methods include a reverse transcriptase-mediated ligase chain reaction (RT-LCR), which has utility similar to RT-PCR. RT-LCR relies on reverse transcriptase to generate cDNA from mRNA, then DNA ligase to join adjacent synthetic oligonucleotides after they have bound the target cDNA.

Hybridization analysis is a preferred method of analyzing the amplification products, employing one or more marker-specific probe(s) that, under suitable conditions of stringency, hybridize(s) with single stranded marker-specific nucleic acid amplification products comprising complementary nucleotide sequences. The amplification products are typically deposited on a substrate, such as a cellulose or nitrocellulose membrane, and then hybridized with labeled marker gene-specific probe(s), optionally after an electrophoresis. Conventional dot blot, Southern, Northern, or fluorescence in situ (FISH) hybridization protocols, in liquid hybridization, hybridization protection assays, or other semi-quantitative or quantitative hybridization analysis methods are usefully employed along with the marker gene-specific probes of the present invention.

Alternatively, electrophoresis for analyzing amplification products is done rapidly and with high sensitivity by using any of various methods of conventional slab or capillary electrophoresis, with which the practitioner can optionally choose to employ any facilitating means of nucleic acid fragment detection, including, but not limited to, radionuclides, UV-absorbance or laser-induced fluorescence. (K. Keparnik et al., *Fast detection of a (CA)18 microsatellite repeat in the IgE receptor gene by capillary electrophoresis with laser-induced fluorescence detection*, Electrophoresis 19(2);249–55 [1998]; H. Inoue et al., *Enhanced separation of DNA sequencing products by capillary electrophoresis using a stepwise gradient of electric field strength*, J. Chromatogr. A. 802(1):179–84 [1998]; N.J. Dovichi, *DNA sequencing by capillary electrophoresis*, Electrophoresis 18(12–13):2393–99 [1997]; H. Arakawa et al., *Analysis of single-strand conformation polymorphisms by capillary electrophoresis with laser induced fluorescence detection*, J. Pharm. Biomed. Anal. 15(9–10):1537–44 [1997]; Y. Baba, *Analysis of disease-causing genes and DNA-based drugs by capillary electrophoresis. Towards DNA diagnosis and gene therapy for human diseases*, J. Chromatgr B. Biomed. Appl. 687(2):271–302 [1996]; K. C. Chan et al., *High-speed electrophoretic separation of DNA fragments using a short capillary*, J. Chromatogr B. Biomed. Sci. Appl. 695(1): 13–15 [1997]).

Any of diverse fluorescent dyes can optionally be used to label probes or primers or amplification products for ease of analysis, including but not limited to, SYBR Green I, Y1O-PRO-1, thiazole orange, Hex (i.e., 6-carboxy-2',4',7', 4,7-hexachlorofluoroscein), pico green, edans, fluorescein, FAM (i.e., 6-carboxyfluorescein), or TET (i.e., 4,7,2',7'-tetrachloro-6-carboxyfluoroscein). (E.g., J. Skeidsvoll and P.M. Ueland, *Analysis of double-stranded DNA by capillary electrophoresis with laser-induced fluorescence detection using the monomeric dye SYBR green I*, Anal. Biochem. 231(20):359–65 [1995]; H. Iwahana et al., *Multiple fluorescence-based PCR-SSCP analysis using internal fluorescent labeling of PCR products*, Biotechniques 21(30:510–14, 516–19 [1996]).

The preceding are merely illustrative of useful techniques that can be employed to detect the one or more physiological and/or immunological features of an endothelial precursor cell, such as the expression of a marker of interest. Other suitable techniques can alternatively be employed.

After selection of the endothelial sprout cell(s)(i.e., a first endothelial sprout cell), and/or of cells having at least one physiological and/or immunological feature of endothelial precursor cells, from the basement membrane matrix (i.e., from the expansive culture conditions), as described above, still further enrichment of a cell population for endothelial sprout cells and/or endothelial precursor cells can, optionally, be achieved with additional subculturing under differentiative culture conditions. Optionally, a successive cycle of alternating expansive culture conditions/differentive culture conditions is useful. If the proliferating endothelial sprout cells and/or EPCs that are selected from expansive culture conditions are directly subcultured to expansive culture conditions (in fresh medium), they eventually reach a proliferative plateau when further cell division ceases, i.e., proliferation ceases, typically within about one month after tube collapse.

Preliminary studies (data not shown) using the inventive method have indicated that cells subcultured from expansive culture conditions to differentivative culture conditions become negative for the expression of EPC-specific markers, just as the primary cells were that had not yet been cultured under expansive culture conditions on the first basement membrane matrix. Further studies show that cells subcultured under differentiative culture conditions, after being selected from expansive culture conditions, have the typical flattened morphology of mature endothelial cells instead of the characteristic elongated, spindle-like (i.e., "sprout") morphology of endothelial sprout cells originally observed under expansive culture conditions. Only endothelial cells in primary cell cultures, and endothelial cells subcultured from differentiative culture conditions, are able to form tubes under expansive culture conditions. Endothelial sprout cells selected from expansive culture conditions and subcultured directly into fresh medium under expansive culture conditions maintain the undifferentiated "sprout" morphology and do not form tubes.

In the first culturing under expansive culture conditions, in accordance with the method, cell viability is reduced by 95% immediately after tube collapse and before sprouting colonies have begun to develop. In this first round, under expansive culture conditions, the remaining viable cells typically proliferate abundantly to yield an expanded population of cells about 200–300 times the original viable cell number after tube collapse, if, optionally, one or more angiogenic growth factors is added to the liquid medium (e.g., platelet derived growth factor [PDGF]-BB, fibroblast growth factor [FGF]-2, vascular endothelial growth factor [VEGF], insulin-like growth factor [IGF]-I, and/or placental growth factor [PlGF]). However, in each successive cycle of subculturing under differentiative and then expansive culture conditions, cell viability immediately after tube collapse increases, until by the fifth subculturing under expansive culture conditions, cell viabilty immediately after tube collapse has been observed at about 53%. Even without the addition of angiogenic growth factors to the medium under expansive culture conditions, after five (expansive/differentive) cycles a subculture returned to expansive culture conditions is at least ten-fold enriched for endothelial sprout cells and/or endothelial precursor cells.

Thus, a population of endothelial sprout cells and/or endothelial precursor cells selected in accordance with the inventive method is optimally further expanded by one or more cycles of culturing under expansive culture conditions and differentiative culture conditions in succession. For the purpose of further expansion of the population of endothelial sprout cells and/or endothelial precursor cells, a particular embodiment of the inventive method further involves subculturing one or more of the selected endothelial sprout cells and/or EPCs, under differentiative culture conditions, on a surface other than a basement membrane matrix (e.g., plastic or glass tissue/cell culture plates), to obtain a population of non-proliferating endothelial cells. Then, one or more of these non-proliferating cells subcultured under differentiative culture conditions are further subcultured under expansive culture conditions with fresh medium and on a fresh (i.e., a second, third, fourth, fifth, etc.) basement membrane matrix, and tube formation is allowed to occur under the expansive culture conditions. After tube collapse, endothelial sprout cells (i.e., a second endothelial sprout cell) and/or cells having one or more physiological and/or immunological features of endothelial precursor cells are selected from sprouting colonies, as described hereinabove. This cycle can be be repeated at least five or more times, if desired, to obtain a population of cells further enriched for endothelial sprout cells and/or endothelial precursor cells (or cells having one or more physiological and/or immunological features of endothelial precursor cells). The addition of PDGF to the culture medium increases the proportion of EPCs obtained in the population.

Subculturing can involve aseptically placing in, or inoculating, fresh medium with at least one cell, and typically involves placing a plurality of two or more cells in the fresh medium, depending on whether a monoclonal or polyclonal culture is desired. For convenience, the inoculum is about $10^3$ to about $10^5$ cells, depending on the size of the culture dish, plate, well, bottle, or other culture receptacle used; e.g., about $5 \times 10^3$ cells per well of a 96-well culture plate is a typical convenient number of cells per inoculum (conveniently delivered by 200-µL micropipette). Typically, a single secondary sprouting colony is about $5 \times 10^3$ cells (approximate size of the smallest secondary sprouting colony visible to the unaided eye) to about $5 \times 10^4$ cells.

A population of endothelial sprout cells and/or EPCs obtained by practicing one or another embodiment of the inventive in vitro method of isolating and expanding a cellular population enriched for cells having one or more physiological and/or immunological features of endothelial precursor cells, can be reinfused into organs/circulation after vascular injury to repair damaged tissue or administered after chemotheraphy, e.g., to an immunosuppressed or immunocompromised patient, or to a patient with another type of blood-vessel ablation trauma, to reconstitute the vasculature. Cell populations enriched for EPCs can be directly injected into tissues prone to ischemia, such as the spinal cord, brain, heart (e.g., intracoronary, intramyocardial, or epicardial injection), bone marrow, liver spleen, uterus, glands, colon, skin (e.g., after burns or other injuries to stimulate the production of growth factors favoring the division of endothelial cells and angiogenesis), joints, tendons, and cartilage. Intraperitoneal and intramuscular injection, and delivery by eye drop formulation are also useful means of adminstration of cell populations enriched for EPCs.

Also, it is a benefit that the EPCs obtained by the inventive method can be used in tissue engineering protocols to give rise to blood vessels that can be then engrafted into an organism. Another benefit is that the EPCs obtained by the inventive method of can be used as vectors for the delivery of genes, proteins or other molecules to the vasculature (since they home-in and incorporate into existing vessels or create new ones). The EPCs can be administered by injection, preferably transvascularly (e.g., intravenously or intrarterially). Alternatively the EPCs can be administered intraocularly (e.g., intravitreously, subretinally, or choroidally) or in an eye drop formulation.

In other applications, EPCs can be genetically modified in vitro, as $CD34^+$ endothelial cells have been previously, to express toxins on their surface and be infused into cancer patients. (E.g., Arafat W O et al., *Genetically modified CD34+ cells exert a cytotoxic bystander effect on human endothelial and cancer cells*, Clin Cancer Res. 6(11):4442–8 [2000]; Cioffi L et al., *A novel endothelial cell-based gene therapy platform for the in vivo delivery of apolipoprotein E*, Gene Ther 6(6):1153–9 [1999]; Gomez-Navarro J et al., *Genetically modified CD34+ cells as cellular vehicles for gene delivery into areas of angiogenesis in a rhesus model*, Gene Ther. 2000 Jan. 7(1):43–52 [2000]). It is well known that EPCs can home-in or exclusively incorporate into active angiogenesis areas, such as tumor neovasculature. (e.g., Voermans C et al., *Homing of human hematopoietic stem and progenitor cells: new insights, new challenges?* J Hematother Stem Cell Res. 2001 Dec.; 10(6):725–38 [2001]; Moore M A, *Cytokine and chemokine networks influencing stem cell proliferation, differentiation, and marrow homing*, J Cell Biochem Suppl 2002, Suppl 38:29–38 [2002]; Mohle R et al., *The role of endothelium in the regulation of hematopoietic stem cell migration*, Stem Cells. 16 Suppl 1:159–65 [1998]; Mazo I B et al., *Adhesion and homing of blood-borne cells in bone marrow microvessels*, J Leukoc Biol. 1999 Jul.;66(1):25–32 [1999]; Papayannopoulou T et al., *Homing and trafficking of hemopoietic progenitor cells*, Acta Haematol. 1997;97(1–2):97–104 [1997]). Consequently, such genetically modified EPCs can be used to target and selectively destroy malignant tumors.

The present invention is also directed to an in vitro method for a screening a substance for potential proangiogenic or antiangiogenic activity. Examples of agents that can be evaluated for potential antiangiogenic activity in accordance with the invention, include compounds or substances, whether or not these are newly known, isolated or synthesized; mixtures of compounds, such as cell, bacterial, fungal, plant or animal extracts; or any combination of these.

Culturing or subculturing of mammalian cells, including endothelial cells, endothelial sprout cells, and/or EPCs, is done by known cell culture techniques, typically by culturing in commercially available liquid aqueous cell culture medium in tissue culture flasks or multi-welled plates, using aseptic techniques. Incubation is generally done at 37° C., in air containing 5% $CO_2$. Optionally, the cells can be cultured in the presence of exogenously supplied signal molecules. "Signal molecules" are cytokines, growth factors, or hormones that can be introduced exogenously to induce or suppress a physiological response of the cells, for example, cell proliferation. Useful examples of signal molecules that induce proliferation of the cells include vascular endothelial growth factor (VEGF), placenta growth factor (PlGF), insulin-like growth factor (IGF)-I, platelet-derived growth factor (PDGF)-BB, epidermal growth factor (EGF), fibroblast growth factor (FGF)-2, and the like, e.g., interleukin, growth hormone (GH), interferon, hepatocyte growth factor (HGF), tumor necrosis factor(TNF)-α, and/or transforming growth factor (TGF)-α. Preferably, but not necessarily, combinations of different signal molecules are employed to yield a synergistic inductive effect, e.g., VEGF+IGF-I; VEGF+IGF-I+FGF-2+PlGF, or the like.

Appropriate controls for use in the in vitro screening method will be self-evident to the skilled artisan. Alternatively, such controls can include: (1) a cell population receiving the potential proangiogenic or antiangiogenic agent in the absence of exogenously supplied signal molecule(s); (2) a cell population receiving the potential proangiogenic or antiangiogenic agent in the presence of exogenously supplied signal molecule(s); (3) a population of cells administered sterile aqueous culture medium (or appropriate vehicle) alone in the presence of exogenously supplied signal molecules; (4) a population of cells administered sterile aqueous culture medium (or appropriate vehicle) alone in the absence of exogenously supplied signal molecules; and/or (5) positive or negative controls employing known proangiogenic or antiangiogenic agents. Other useful negative, positive, and internal controls will be apparent to the skilled artisan.

In the examples presented hereinbelow, an embodiment of the inventive in vitro screening method is illustrated in the screening of CK2 inhibitors for potential antiangiogenic activity. An inhibitor of protein kinase CK2 ("CK2" or "CKII"; EC 2.7.1.37), which is also known as "casein kinase II". (See, e.g., Niefind, K. et al., *Crystal Structure of Human Protein Kinase CK2: Insights Into Basic Properties of the CK2 Holoenzyme*, EMBO J. 20 pp. 5320 [2001]). An inhibitor of protein kinase CK2 is a substance, such as a compound, the selective binding of which, in vivo or in vitro, to a site on CK2 results in a reduction of CK2 enzymatic activity, compared to an appropriate control that lacks the substance. In one embodiment, the inhibitor of protein kinase CK2 ("CK2 inhibitor") is 5,6-dichloro-1-β-D-ribofuranosylbenzimidazole ("DRB"). Alternatively, the CK2 inhibitor is emodin (3-methyl-1,6,8-trihydroxyanthraquinone or 6-methyl-1,3,8-trihydroxyanthraquinone; Beilstein Registry Number: 1888141). Another embodiment is aloe-emodin (1,8-dihydroxy-3-hydroxymethylanthraquinone). Another embodiment of the CK2 inhibitor is 4,5,6,7-tetrabromobenzotriazole (i.e., 4,5,6,7-tetrabromo-2-azabenzimidazole; "TBB"; e.g., Sarno, S et al., FEBS Lett 496(1):44–48 [2001]; Battistutta, R et al., Protein Sci. 10(11):2200–06 [2001]). Also included among useful CK2 inhibitors are pharmaceutically acceptable molecular conjugates or salt forms of emodin, aloe-emodin, DRB, or TBB, that still have activity as CK2 inhibitors as defined herein, and do not impart unacceptable toxicological effects.

While the invention has been described with reference to its preferred embodiments, it will be appreciated by those skilled in this art that variations may be made departing from the precise examples of the methods and compositions disclosed herein, which, nonetheless, embody the invention defined by the following claims.

EXAMPLES

Example 1

Synergistic Effects of Angiogenic Growth Factors on Cultured Retinal Endothelial Cells (REC)

Alterations of angiogenic growth factors and retinal basement membranes (BMs) are important for diabetic retinopathy (DR) pathogenesis. Consequently, whether angiogenic growth factors can mediate angiogenic behavior of retinal endothelial cells (REC) in an additive manner was examined.

Human REC (from normal, diabetic and patients with DR ["DR REC"]) and bovine REC were cultured in monolayer (for migration assay) or on top of MATRIGEL™ biological cell culture substrate where cells form capillary-like tubes. They were treated with angiogenic growth factors or their combinations (at 10 ng/mL of each factor), and seeded with or without TN-C at 10–50 μg/mL. Cell numbers were determined by MTS assay (Promega Corp., Madison, Wis.). Tube length and number, and cell migration were assessed microscopically.

Retinal endothelial cells were isolated from fresh bovine eyes (Sierra for Medical Science, Santa Fe Springs, Calif.) using a modification of the method of Grant and Guay. (Grant and Guay, *Plasminogen activator production by human retinal endothelial cells of nondiabetic and diabetic origin*, Invest. Ophthalmol. Vis. Sci. 32, 53–64 [1991]). For some experiments, human REC were cultured from healthy and diabetic donor eyes obtained from the National Disease Research Interchange (NDR1, Philadelphia, Pa.). NDR1 has a human tissue collection protocol approved by a managerial committee and subject to National Institutes of Health oversight. Briefly, aseptically dissected retinas were manually triturated and passed through a sterile 45 μm nylon mesh (Tetko Inc./Sefar America Inc., New York, N.Y.) followed by extensive rinsing with dissecting buffer [50% fetal calf serum (Omega Scientific Inc., Tarzana, Calif.) in Dulbecco's PBS (Invitrogen/Life Technologies, Carlsbad, Calif.)]. The pooled retentate was digested with collagenase (Worthington Biochemical Corp., Lakewood, N.J.) in $Ca^{++}/Mg^{++}$-free PBS (Invitrogen) with moderate stirring for ~30 min. The digest was resuspended in incomplete REC medium [50% F-12, 50% low-glucose DMEM with antibiotics/antimycotics (Invitrogen) and 10% fetal calf serum (FCS)] and centrifuged at 400×g for 5 min. The pellet was resuspended in high serum, complete, BREC medium [same as incomplete medium plus ITS (insulin/transferrin/selenium), ECGS (endothelial cell growth supplement), all from Sigma-Aldrich Co., St. Louis, Mo., and 20% FCS]. After the first passage cells were routinely cultured in complete BREC medium with 10% FCS (growth medium). Only passages 3–7 were used for experiments. Cultures were often checked for purity by immunostaining with a rabbit polyclonal antibody against von Willebrand factor (Sigma-Aldrich).

In vitro MATRIGEL™ biological cell culture substrate assay of capillary-like tube formation and secondary sprouting. BD or GFR MATRIGEL™ biological cell culture substrate, basement membrane matrix formulations are derived from a tumor extract containing major basement membrane components (10 mg/mL protein), which preparations were found to be superior over three other brands in terms of tube formation. Briefly, 50 μL of reconstituted basement membrane matrix from mouse EHS tumor (BD or GFR MATRIGEL™ biological cell culture substrate; Becton Dickinson Labware, Bedford, Mass.) were dispensed with frozen pipettes into each well of a previously frozen, sterile 96-well plate sitting on wet ice and allowed to solidify for 1 hr at room temperature or 37° C. Approximately $5 \times 10^4$ or $7.5 \times 10^4$ REC in a 100 μL volume were seeded into each triplicate well. Human recombinant or purified growth factors were added to a final concentration of 10 ng/mL (or as noted) in 0.5% FCS incomplete BREC medium. Capillary-like tube structures formed by REC on reconstituted basement membrane matrix were photographed at various intervals ranging from 12–72 hr; pictures were scanned, digitized and analyzed using image-processing software.

For the secondary sprouting assay, cells on reconstituted basement membrane matrix were seeded as above but incubated in 0.5% FCS incomplete BREC medium without any growth factors for 3 days, allowing for tube formation and collapse. On day 3, human recombinant or purified growth factors were added to a final concentration of 10 ng/mL (or as noted) in low-serum incomplete BREC medium and incubated for another 5–6 days. Digital photographs were obtained with a Kodak MDS 100 camera attached to a Leitz DM IL inverted microscope. Digitized images obtained with a Kodak MDS 100 video camera were stored on compact discs and quantified with NIH Image 1.62 software. The number of living cells in the sprouting colonies were determined using the MTS cell proliferation assay.

The cells form tubes on MATRIGEL™ biological cell culture substrate by 16 hr, and by 48 hr, without TN-C or growth factors, the tubes collapse. Secondary sprouting with MATRIGEL™ biological cell culture substrate invasion starts by day four in culture. Cultures were monitored microscopically. Culture medium with or without growth factors or inhibitors was changed every two-three days.

Migration assay. REC migration rates were examined in a wound healing assay, where cells migrate over time into the scrape wound in a monolayer. Briefly, cells were seeded in 24-well plates and allowed to reach confluence in growth medium. Prior to growth factor treatment, cells were serum-starved overnight in incomplete BREC medium with 0.5% FCS. All monolayers within an experiment were wounded with a single sterile wood stick of constant diameter, to ensure uniformity in the wound areas among different treatments. Wounded monolayers were then rinsed with low-serum medium to remove detached cells and treated with various combinations of human growth factors at 10 ng/mL each. On day 7, cells were rinsed 3× with PBS and fixed with methanol for 15 min, rehydrated with $dH_2O$ and stained with Meyer's hematoxylin for 5 min, followed by destaining with $dH_2O$. All wells were photographed with a 4× or 10× objective using a Kodak MDS 100 digital camera attached to a Leitz DM IL inverted microscope. The original wound area was measured at 0 hr and used as a baseline for comparison to the treated wells at the conclusion of the experiment. The number of cells migrated into the wound was determined. Migrating cell counting was automated using the AAB (Advanced American Biotechnology, Fullerton, Calif.) software. Data were calculated and statistically analyzed (Spirin K S et al., *Basement membrane and growth factor gene expression in normal and diabetic human retinas*, Curr. Eye Res. 18:490–499 [1999]) relative to control cultures that received the same concentrations of bovine serum albumin instead of growth factors and/or inhibitor, compared to vehicle instead of inhibitor after wounding. Inhibitors were added 30 min before growth factors.

REC proliferation and survival assays. 96-well plates were coated with various amounts of TN-C or vehicle. $5 \times 10^3$ cells were added to each triplicate well in low-serum REC medium with various amounts of growth factors (0.5% FCS incomplete BREC medium containing 10 ng/ml of human IGF-I, FGF-2, VEGF, PlGF and PDGF-BB [R&D Systems Inc., Minneapolis, Minn.]). Cell numbers were determined on days 4–7 using the MTS cell proliferation assay (Promega Corp.) according to manufacturer's instructions. Survival was measured in the same way using high glucose (30 mM) or chemical hypoxia (2 mM sodium azide) or serum-free medium to induce cell death. Cell numbers were determined on days 4–7 using MTS assay (Promega).

Immunohistochemistry. Secondary sprouting colonies were scooped out of the reconstituted basement membrane matrix, washed with Dulbecco's PBS (Invitrogen) and embedded in OCT (Ted Pella Inc., Redding, Calif.). Blocks were frozen and cryosectioned. Some slides were stained with hematoxylin and eosin using standard protocols in order to locate the sprouting colonies within pieces of matrix. Unfixed 5-μm sections were double stained with a rabbit polyclonal antibody against von Willebrand factor (Sigma) and a rat monoclonal antibody against the laminin γ1 chain, clone A5 (Ljubimov et al., *Distribution of individual components of basement membrane in human colon polyps and adenocarcinomas as revealed by monoclonal antibodies*, Int. J. Cancer 50:562–6[1992]), at 20 μg/mL for one hour at room temperature. Slides were washed extensively with PBS and incubated for another hour with a 1:80 dilution of their respective cross-species preabsorbed secondary antibodies (Chemicon International, Temecula, Calif.) coupled to fluorescein or rhodamine. After extensive washing, slides were mounted in 50% glycerol in PBS and photographed using an Olympus BH-2 fluorescent microscope.

Image and Statistical Analysis. All the treatment data sets were individually compared to their respective controls (unless otherwise specified) by the paired Student's t-test using the GraphPad Prism 3.0 program (GraphPad Software, San Diego, Calif.). In some experiments, one treatment was compared to several others using a non-parametric one-way ANOVA test (GraphPad Software). Tube formation images were processed by background subtraction, thresholding and measurement of total length of tubes using Adobe Photoshop v5.0 (Adobe Systems Inc., San Jose, Calif.) and the Image Processing Toolkit v3.0 (Reindeer Games, Inc., Gainesville, Fla.).

Treatment of REC cultures. Duplicate REC cultures on plastic (for migration) or MATRIGEL™ biological cell culture substrate with the same number of cells per dish are treated with previously established working concentrations of signaling inhibitors and/or select growth factor combinations. Treatments begin at the time of seeding the cells and medium is changed every other day. Single growth factors are used as negative controls since their modulation of TN-C effects was minimal. Working growth factor concentrations were as follows: VEGF, 1–50 ng/mL depending on the assay; PlGF, 100 ng/mL; FGF-2, 10–100 ng/mL; IGF-I, 25–100 ng/mL; PDGF-BB, 10–100 ng/mL. When used as combinations, each growth factor was supplied at 10 ng/mL for optimum synergy. The already tested inhibitors of signaling molecules (Sigma, Calbiochem, BIOMOL) were used at the following optimized doses: protein kinase A (inhibitor: H89 [25 μM]), PKC (inhibitor: calphostin C [2.5 μM]), PKC-β (inhibitor: LY379196 [50 nM]), $Ca^{2+}$/calmodulin kinase II (inhibitor: KN-93 [0.5 μM]), CK1 (inhibitor: CKI-7 [50 μM]), MEK-ERK (inhibitor: PD98059 [10 μM]), p38 MAP kinase (inhibitor: SB202190 [10 μM]), PI3 kinase (inhibitor: wortmannin [100 nM]), CK2 (inhibitors: emodin [20–25 μM] and DRB [20–25 μM]), CK2 and other kinases (inhibitor: quercetin [50 μM]); and a negative control for kinase inhibition (SB202474 [10 μM]). In some experiments cells were grown in hyperglycemic medium with 30 mM glucose.

Example 2

Synergistic Effects of Growth Factors on Angiogenic Cellular Behaviors

Figure 1:
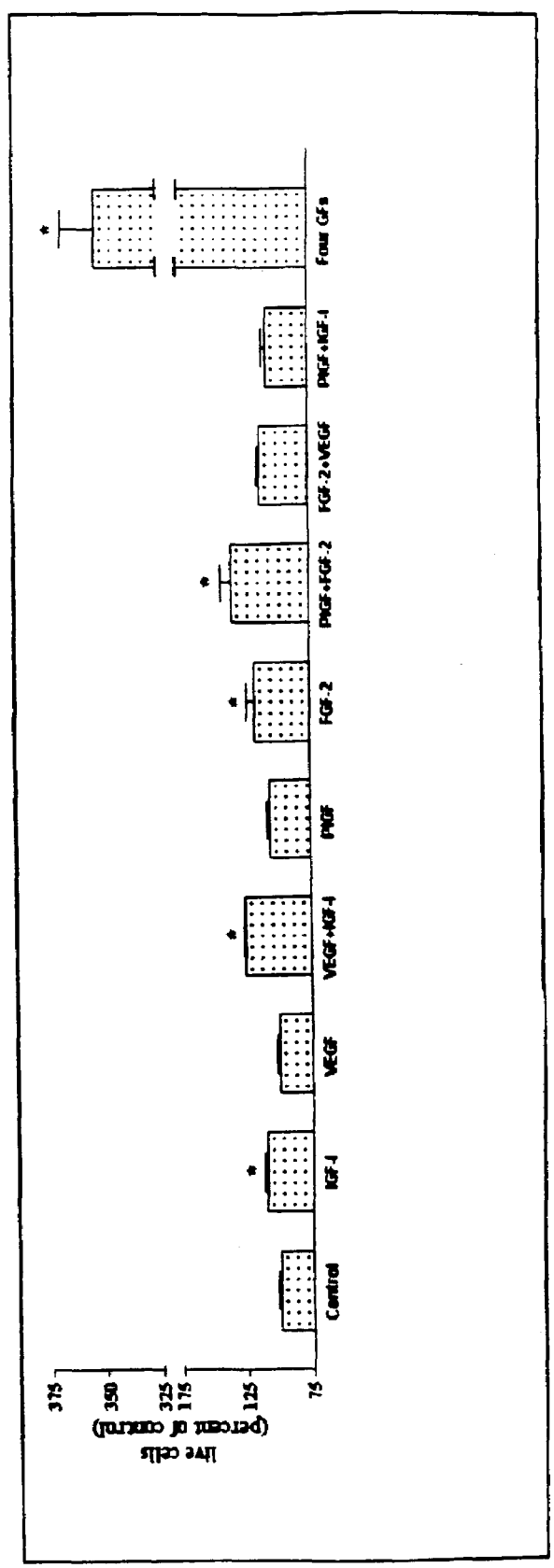
FIG. 1 shows synergistic growth factor-mediated increase of retinal endothelial cell (REC) proliferation. Bovine REC were treated for 6 days with—10 ng/mL each of the indicated growth factors (GFs) in medium with 0.5% serum. Cell numbers were measured with MTS assay. Note a dramatic threefold increase of cell number after treatment with a combination VEGF+IGF-I+FGF-2+PlGF ("Four GFs") compared to single or paired growth factors. Bars are mean±SEM of at 3–7 experiments in triplicate. *, p<0.05 vs. control.

It was found that growth factors synergized to promote REC angiogenic behavior. Growth factor activities were rather selective. IGF-I preferentially synergized with VEGF, but FGF-2 coupled with PlGF (FIG. 1). PDGF-BB had a slight preference for FGF-2. However, it was so potent in REC by itself, that other factors only mildly enhanced its action. Individual growth factor effects on REC behavior varied. For example, VEGF had little effect on REC survival but significantly enhanced migration. IGF-I was the opposite. However, VEGF+IGF-I exerted an additive effect on cell survival, tube formation, sprouting, migration, and proliferation. REC treated with combinations of four or five growth factors showed significant, several-fold, enhancement of most angiogenic parameters tested (FIG. 1). Therefore, some angiogenic responses may be triggered only by growth factor combinations.

Vascular damage in DR is followed by angiogenic burst that creates a network of leaky and fragile vessels. We detected a similar process in REC cultured on basement membrane matrix (e.g., BD or GFR MATRIGEL™ biological cell culture substrate). It was known that endothelial cells plated on basement membrane matrix stopped proliferating, formed capillary-like hollow tubes for 24–48 hr did not invade the matrix, collapsed into clumps, and died (Benelli R, Albini A, *In vitro models of angiogenesis: the use of Matrigel*, Int. J. Biol. Markers 14:243–246 [1999]). This was heretofore thought to be the endpoint of the assay. However, it was observed, as described herein, that some cells survive following tube collapse. They 1) proliferate, 2) migrate, 3) form spherical colonies that remain alive for weeks, 4) invade basement membrane matrix (e.g., BD MATRIGEL™ biological cell culture substrate or GFR MATRIGEL™ biological cell culture substrate), and 5) can reassemble into larger tubes. Cells from these sprouting colonies, which arise predominantly, but not necessarily (given the migratory capacity of the endothelial sprout cells), in the nodes of intersecting collapsed tubes (to which collapsing tubes tend to retract), and sometimes at other sites in or on the collapsed tubes, are microscopically observed to possess elongated morphological processes about 50 to about 500 micrometers long, i.e., "sprouts", one or two of which extend from a single individual cell. One or more of these endothelial sprout cells can be selected in accordance with the present invention.

FIG. 2 E–H, shows that surviving BREC 1) proliferate, 2) migrate (form secondary sprouts), 3) organize into spherical, three-dimensional colonies that remain alive for weeks, 4) invade the matrix, and 5) may connect and reassemble into larger tubes (FIG. 2, panels E and F). This process, named herein "secondary sprouting", to distinguish it from the sprouts that form immediately after seeding cells on reconstituted basement membrane matrix prior to and during tube formation. The secondary sprouting phenomenon recapitulates various consecutive steps in the angiogenic process and is potently stimulated by angiogenic growth factors, such as PDGF-BB and FGF-2 (FIG. 2, panels G and H). Interestingly, the morphology of the sprouting colonies after treatment with these growth factors is slightly different, with PDGF-BB stimulating shorter and thicker sprouts, whereas FGF-2 induces longer and sparser sprouts. As observed, this assay provides a novel method for testing the effects of a diverse range of compounds, including growth factors, on REC survival, proliferation, tube formation, migration and invasion in a single experiment.

Studies were performed aimed at characterizing this process as well as the nature of the surviving cell population. The sprouting colonies were comprised of endothelial cells since they were all positive for a specific endothelial cell marker, von Willebrand factor (FIG. 12). FIG. 12 also shows that the basement membrane matrix, visible using antibodies against a ubiquitous gamma1 chain of laminin (a major component of this matrix), surrounds the sprouting cords of von Willebrand factor-positive cells (FIG. 12, bottom row). These experiments also demonstrated the formation of lumens containing more than six cells, which were positive for von Willebrand factor (FIG. 12, top row). It was found that human retinal endothelial cells behaved similarly to their bovine counterparts in the secondary sprouting assay (FIG. 12, bottom row). This suggests that the secondary sprouts were not comprised of trans-differentiated endothelial cells or contaminating cells remaining from the original primary cultures. Further immunological and biological characterization of sprouting colonies is currently underway.

A good correlation was observed between the spherical volume and the number of live cells in secondary sprouting colonies (not shown). Since the latter is an easy parameter to test by using the MTS assay, it was adopted as a faster method for studying the effect of various agents on secondary sprouting.

Given the fact that secondary sprouting appears to recapitulate various steps of angiogenesis, it was not surprising to find that growth factors exerted significant influence on this process. As seen in FIG. 13, the number of living cells in the secondary sprouting cultures exposed to single or combined growth factors generally imitated the pattern observed for BREC proliferation/survival (See, e.g., FIG. 1). Again, 'matched' growth factor pairs were more active in stimulating secondary sprouting than individual factors or 'mismatched' pairs. A cocktail containing PlGF, IGF-I, FGF-2 and VEGF was more potent in stimulating BREC secondary sprouting than individual or paired growth factors.

In particular, secondary sprouting was stimulated on average three-fold by PDGF-BB and four-fold by FGF-2, whereas other individual factors were less potent. Growth factor combinations were again more effective than individual factors: VEGF+IGF-I, 150%, PlGF+FGF-2, five-fold, and all these four factors, up to six-fold. Basal and growth factor-enhanced secondary sprouting could be decreased by inhibitors of CK2 but not of several other key signaling molecules. It was also observed that DM and DR REC exhibited a higher sprouting ability than normal REC.

PDGF-BB demonstrated unique behaviors in the secondary sprouting assay. When added at the time of cell inoculation, it was the most potent single growth factor and as potent as any tested growth factor pair (FIG. 13). This effect might be due to its known ability to promote cell survival/proliferation at the tube collapse phase. Therefore, it was essential to determine if PDGF-BB (or other growth factors in combination) would display an activity in this assay independently of its influence on cell survival during tube collapse. To test this possibility, we next added growth factors to the cultures after the tubes had collapsed, and PDGF-BB again increased secondary sprouting, similar to the effect shown on FIG. 13 when it was added prior to tube collapse. Moreover, its action was not additive or synergistic with individual growth factors (FIG. 14A). At the same time, when IGF-I, VEGF and FGF-2 were present, addition of increasing doses of PDGF-BB potentiated their responses (FIG. 14B). No other growth factors were capable of exerting additive or synergistic effects with combinations of three other growth factors under these conditions (FIG. 14B). Surprisingly, FGF-2, which has been described as angiogenic throughout the literature, demonstrated 'pro-angiogenic' effects in the secondary sprouting assay (FIG. 13 and FIG. 14A) but had little or no effect on tube formation or cell migration (data not shown). Similarly, PDGF-BB, which is a potent stimulator of cell migration, proliferation and sprouting was actually a pro-collapsing factor in the tube formation assay (data shown). These results also validated the use of the secondary sprouting assay to determine the angiogenic capacity of individual or combined growth factors, which may not be revealed by more traditional methods such as tube formation or cell migration assays.

FIG. 4 shows the effect of DRB on bovine REC proliferation and survival. Cells were plated in medium with 0.5% (survival) or 10% serum (proliferation) containing various concentrations of DRB. The number of live cells was measured on day 6 with MTS assay. Bars represent mean±SDEM of two individual experiments in triplicate. The results show that DRB significantly lowers cell number at both serum concentrations.

FIG. 5 shows the effect of DRB on bovine REC secondary sprouting. Cells were seeded on MATRIGEL™ biological cell culture substrate in medium with 0.5% serum containing various concentrations of DRB. The number of live cells was measured on day 9 with MTS assay. Bars represent mean±SDEM of two individual experiments in duplicate. The results show that DRB significantly decreases cell number starting at 25 µM.

Example 3

Gene Array Analysis of Growth Factor Action on Normal REC and DR REC

Normal REC and DR REC gene expression patterns were compared by gene array analysis. Normal, diabetic and DR autopsy human eyes are obtained from National Disease Research Interchange (NDRI), within 24 hours after death. These eyes are used to isolate REC for culture as described hereinabove. Cultures can be used up to the fourth passage, and viable cultures can be cryogenically stored. Cultures of normal, diabetic and DR REC are established from autopsy human eyes and routinely checked for purity using von Willebrand factor immunostaining as described hereinabove. Cells are cultured in 50% F-12, 50% low-glucose DMEM with antibiotics/antimycotics (GIBCO/BRL), insulin-transferrin-selenite, ECGS (Sigma Chemical Co.), and 20% FCS. Statistical analysis of results is done with Graph-Pad Prism software (GraphPad Software).

In experiments, normal, diabetic, and DR REC were grown for seven days with or without 10 ng/ml VEGF, or 10 ng/mL IGF-I, or 10 ng/mL each VEGF and IGF-I, in medium with 0.5% serum. Long-term rather than short-term treatment was chosen because diabetes develops over a considerable time period. RNA isolated from REC was reverse-transcribed using Smart™ cDNA synthesis method (Clontech), to produce full-length cDNA. Two normal cases or two DR cases were pooled together. This cDNA was PCR-amplified with a short number of cycles and used as a probe for Clontech Atlas Human 1.2 1,200-gene arrays, according to the manufacturer's instructions. This technique had previously been refined and verified by Northern analysis and fully correlated gene array data with protein expression. (Spirin K S et al., *Analysis of gene expression in human bullous keratopathy corneas containing limiting amounts of RNA*, Invest. Ophthalmol. Vis. Sci. 40:3108–3115 [1999]). Samples were normalized to several housekeeping genes and the analysis was done with available AtlasImage 2.0 software (Clontech). Signal ratio >2 between samples was considered significant as per manufacturer's recommendation.

The gene expression pattern of untreated DR REC showed relatively increased expression of pro-apoptotic genes (Table 1), in agreement with known apoptosis activation in diabetic retinas (Gerhardinger C et al., *IGF-I mRNA and signaling in the diabetic retina*, Diabetes 50:175–183 [2001]). These included caspases, Fas antigen and ligand, tumor necrosis factor (TNF)-α and its receptors, and bcl-2 killer (BAK). Expression of mRNAs of VCAM-1 and its $\alpha_4$ integrin receptor, related to the activated endothelium, were also elevated. However, some proliferation-related genes (STAT3, c-jun and c-fos protooncogenes, G1/S cyclin E, transcription factors E2F, ets-1, NF-κB, intermediary factor 1β) were also increased compared to normal cells. DR-upregulated ets-1 and NF-κB, which can induce TN-C expression that increases in DR retinas. (E.g., Jones F S, Jones P L, *The tenascin family of ECM glycoproteins: structure, function, and regulation during embryonic development and tissue remodeling*, Dev. Dyn. 218:235–2597 [2000]; Spirin K S et al., *Basement membrane and growth factor gene expression in normal and diabetic human retinas*, Curr. Eye Res. 1999;18:490–499 [1999]). DR REC had increased CK2 and its binding protein, protein phosphatase 2 (PP2A), consistent with a significant role for CK2 in DR development. FIG. 9 shows CK2 α subunit expression in cultured REC of normal (N) and diabetic retinopathic (DR) origin as detected by immunohistochemistry. In normal cells, a comparatively weak nuclear staining is mostly seen. In DR cells, there was also distinct cytoplasmic staining (arrows). The staining intensity was higher in DR cells, indicating overexpression of CK2. Cathepsins decreased in DR REC, in line with previously observed reduced basement membrane proteolysis in DR retinas. (Grant M B et al., *Plasminogen activator inhibitor (PAI)-1 overexpression in retinal microvessels of PAI-1 transgenic mice*, Invest. Ophthalmol. Vis. Sci. 41:2296–2302 [2000]).

Growth factor treatment mostly caused coordinate gene expression changes in normal and DR REC (Table 1). A minority of genes were changed selectively, either in normal or DR cells, and VEGF-treated cells did not display an increase of pro-apoptotic genes (not shown). Certain proliferation-related genes were upregulated by VEGF, including transcription factor Sp2, elongation factors SII and SIII, and signaling molecules, S6 kinase and JAK1. VEGF downregulated various phosphatases in normal and DR REC suggesting activation of phosphorylation-dependent metabolic pathways, while exposure to IGF-I alone caused a decrease of pro-apoptotic genes (not shown). A combination VEGF+IGF-I caused a dramatic downregulation of pro-apoptotic genes (activated in DR) and an increase of proliferation-related genes (data not shown). Particularly, a group of several stress-related MAP kinases associated with endothelial and pancreatic β-cell apoptosis in diabetes (Davis R J, *Signal transduction by the JNK group of MAP kinases*, Cell 103:239–252 [2000]) was also downregulated. At the same time, key signaling molecules, PLCγ2, PI3 kinase α, and ras p120 activator were increased by VEGF+IGF-I.

Gene expression profile of DR REC showed increases of many apoptosis-associated genes (Table 1). CK2 gene expression was elevated in DR cells. Synergistic action of angiogenic growth factors on normal and DR REC gene expression was consistent with other data from cell migration, proliferation, and secondary sprouting (MATRIGEL™ biological cell culture substrate) assays. Moreover, the gene expression data in REC (Table 1) closely parallel the results obtained by other methods not related to gene expression analysis. (Davis R J, *Signal transduction by the JNK group of MAP kinases*, Cell 103:239–252 [2000]; Franklin R A, McCubrey J A, *Kinases: positive and negative regulators of apoptosis*, Leukemia 14:2019–2034 [2000]). Therefore, there is strong reason to believe that the major changes detected by gene arrays translate into gene product changes, significantly including increased CK2 expression in DR REC.

TABLE 1

Gene array analysis of gene expression in human REC cultures from patients with diabetic retinopathy (DR) compared to normal humans.

| Increased Expression in DR vs. Normal | Decreased Expression in DR vs. Normal |
| --- | --- |
| E2F transcription factor 3 | Autocrine motility factor receptor |
| G1/S cyclin E | BMP1 |
| Caspase 3 | EGF |
| Caspase 4 | PAI-1 |
| Caspase 6 | Integrin β3 |
| BCL2 killer (BAK) | BCL2-like 2 |
| Thrombopoietin receptor precursor | MAPK7 |
| Protein-tyrosine phosphatase 1E | Cadherin 14 (M-cadherin) |
| Protein phosphatase 2A | Fas-activated ser/thr kinase |
| Ras-related protein RAP-1A/KREV-1 | IL-5 |
| N-myc protooncogene | L-myc protooncogene |
| Transcription intermediary factor 1β | Cathepsin D |
| CK2 α | Cathepsin C |
| STAT3 | STAT1 |
| IGF-II | Integrin β5 |
| VEGFR3 | |
| FAS antigen | |
| FAS ligand | |
| TNF-α | |
| TNFR superfamily member 1B | |
| TNFR superfamily member 1A | |
| Cell division control protein 2 (CDC2) | |
| c-kit protooncogene | |
| fos-related antigen 2 | |
| jun-D protooncogene | |
| c-jun protooncogene | |
| ets-1 p54 | |
| ets-related gene transforming protein | |
| Microtubule affinity-regulating kinase 3 | |
| Ephrin-B receptor 2 (EPH-3) | |
| VCAM-1 | |
| Integrin α4 | |
| NF-6B | |
| EGFR substrate | |
| MAPK3 | |

Example 4

CK2 Involvement in REC Behavior, Growth Factor Action, and Retinal Neovascularization Methods. In order to facilitate the optimization of CK2 inhibitor doses and the application of various assays, large numbers of bovine REC were employed in some experiments. The bovine REC were very similar to human REC in all assays and in their responses to growth factors. Cultured cells were treated with growth factor combinations with or without inhibitors of the following molecules: protein kinase A (inhibitor: H89), PKC (inhibitor: calphostin C), PKC-β (inhibitor: LY379196), $Ca^{2+}$/calmodulin kinase II (inhibitor: KN-93), CK1 (inhibitor: CKI-7), MEK-ERK (inhibitor: PD98059), p38 MAP kinase (inhibitor: SB202190), PI3 kinase (inhibitor: wortmannin), CK2 (selective inhibitors: emodin and DRB), CK2 and other kinases (inhibitor: quercetin).

Results. Preliminary results had demonstrated that H-7, a broad-spectrum protein kinase inhibitor, stabilized REC tubes on MATRIGEL™ biological cell culture substrate, inhibited secondary sprouting, migration and proliferation (not shown). Consequently, attempts were made to identify specific kinases that were inhibited by H-7 and played a role in these events. Most inhibitors tested caused minor to moderate effects in all assays. However, inhibitors that could block CK2 (quercetin, emodin DRB) potently inhibited basal and growth factor-stimulated proliferation, secondary sprouting, migration, and tube formation (FIG. 5). As emodin and DRB are specific CK2 inhibitors, and other inhibitors had only a slight effect, the observed inhibition by quercetin was most probably due to blocking CK2 activity. Actinomycin D caused only minor changes in angiogenic assays, implying that CK2 effects on REC did not involve its known impact on transcription (e.g., Guerra B, Issinger O G, *Protein kinase CK2 and its role in cellular proliferation, development and pathology*, Electrophoresis 20:391–408 [1999]).

A specific protein kinase CK2 inhibitor, emodin, was tested for its ability to inhibit neovascularization in oxygen-induced retinopathy in newborn mice (7-day old C57BL/6J mouse pups weighing 4–5 g each) in a previously described animal model. (Smith, L E et al., Invest Ophthalmol Vis Sci 35: 101–111 [1994]; Rotschild, T et al., Pediatr Res 1999;46: 94–100). Briefly, these experiments were done as described [Mino R P et al., *Adenosine A2B antagonists reduce retinal neovascularization*, Curr. Eye Res. 2001, In press.]. Wild type C57BL/6J mice (Jackson Laboratory) were used. The retinopathy group was placed in 75% oxygen at postnatal day seven and maintained in these conditions with their nursing mothers for five days. These mice were then returned to normal air and maintained for another five days. Normoxic control mice are maintained in normal air for the same duration as test mice and under the same conditions of light cycle and temperature. Mice were anesthetized with Ketamine-Xylazine (in a ratio 0.1:0.1:0.5 with PBS injected at 5 μL/g body weight) and perfused through the left ventricle with 4% paraformaldehyde in 0.1 M phosphate buffer pH 7.4 with 50 mg/mL $2\times10^6$ Da fluorescein-dextran (Sigma Chemical Co.). The eyes were enucleated and fixed in 4% paraformaldehyde for 18 h. The sclera and retinal pigment epithelium were stripped off the outer surface of the eye with jewelers forceps. The retina was dissected free of the lens and cornea, peripheral retinas are cut in five places and are flat-mounted with glycerol-gelatin. The retinas were viewed by fluorescence microscopy and photographed.

A minimum of 5 mouse pups were used per group. Emodin at 20–30 μg/g of body mass (or 10 μl/g) was prepared as a solution (70% ethanol) or suspension (PEG-Tween) in vehicle. Vehicle ("emodin solvent") was 70% ethanol in initial experiments. In three later experiments, phosphate-buffered saline with 20% polyethylene glycol 400 (PEG 400)+2% Tween-80, pH 7.2, was used as vehicle. The PEG-Tween did not ensure emodin solubility, so the final mixture was a suspension that was sonicated briefly before injections. The latter vehicle proved to be better than 70% ethanol in terms of mouse survival.

Each mouse pup received two intraperitoneal injections of CK2 inhibitor or vehicle control daily. Injections started on the final day of hyperoxia (day 11 after birth) and continued throughout the subsequent normoxic period until the last day of experiment (day 17 after birth). The mice were euthanized as described herein above and their eyes were analyzed quantitatively for the extent of retinal neovascularization by the following method. On the fifth day after return to normoxia, the eyes from perfused mice were fixed in 4% paraformaldehyde and were embedded in paraffin. Serial 1-βm sections of whole eyes were cut sagitally, with 10 μm between sections, through the cornea and parallel to the optic nerve. Ten sections were counted from each eye resulting in sampling thickness of 110 μm in each eye. Sections were stained with hematoxylin-eosin to visualize cell nuclei under light microscopy. Human counters blinded to the treatment identity counted all nuclei above the inner limiting membrane (ILM) in 10 sections per each eye. Neovascularization rate in TN-C null retinas is calculated as the fraction of total nuclei over total nuclei in wild type or heterozygous control. Sections with the optic nerve were excluded, since normal vessels emanating from the optic nerve, though distinguishable from neomicrovasculature extending into the vitreous, fulfill the counting criterion and would have increased the error. Vascular cell nuclei were considered to be associated with new vessels if found on the ILM vitreal side. Pericytes were not identified in the neovascular tufts and have not been documented in neovasculature. Nevertheless, pericytes or their precursors may have been included in some cell counts. Results were statistically analyzed with a two-tailed Student t test using GraphPad Prism software program (GraphPad).

The FIG. 6 shows representative fluorescein angiograms of the retina from a vehicle-treated mouse (FIG. 6A) and of the retina from an emodin-treated mouse (FIG. 6B). There was significantly less vascularization in the emodin-treated mouse retina than in the vehicle control. Arrows show neovascular tufts prominent in the vehicle-treated animals. These tufts were much less pronounced in the emodin-treated pups (FIG. 6B) than the vehicle control group (FIG. 6A).

The FIG. 7 shows a quantitation of preretinal neovascularization in untreated, vehicle-treated and emodin-treated mouse retinas. Paraffin-embedded tissue sections were used and 3–4 sections per mouse eye were counted. Data represent mean of seven separate experiments, with a total of 24–30 mouse pups per group, (n=number of pups). Since the fellow eye (i.e., contralateral eye) of each mouse was stained by fluorescein, each embedded eye represents a separate animal. The results clearly show that emodin drastically diminished retinal neovascularization by 70–75%, with highly significant differences compared to either untreated or vehicle-treated animals (P<0.0001).

Another selective protein kinase CK2 inhibitor, DRB, was used in several experiments and the results were similar to those obtained with emodin, albeit the inhibition of retinal neovascularization was somewhat less pronounced. FIG. 8 shows a quantitation of preretinal neovascularization in untreated, vehicle-treated and DRB-treated mouse retinas. Data represent mean of two separate experiments, with a total of 3–5 mouse pups per group, (n=number of pups). Since the fellow eye (i.e., contralateral eye) of each mouse was stained by fluorescein, each embedded eye represents a separate animal. The results show that DRB diminished retinal neovascularization by about 60%, with highly significant differences compared to either untreated or vehicle-treated animals (P<0.0001).

Together, these data demonstrate that specific inhibitors of protein kinase CK2 are indeed capable of efficiently inhibiting retinal neovascularization in the oxygen-induced mouse retinopathy model. Since it is difficult to inject compounds in the mouse eye, injections were done intraperitoneally. Even with this route of administration, the beneficial effect in the retina was very pronounced. Previous work with a less selective inhibitor, quercetin, also showed substantial effect with intramuscular injections (data not shown). Importantly, the treatment reduced neovascular tufts in the retina, with little, if any effect on pre-existing retinal vasculature, or vasculature in other parts of the body.

Example 5

Further Characterization of Cells Selected from Secondary Sprouting Colonies

Detection of markers expressed by cells selected from secondary sprouting colonies was carried out using reverse-transcriptase polymerase chain reaction (RT-PCR) with RNA derived from secondary sprouting cells, which was compared to RNA derived from non-sprouting cells. The RT-PCR method allows the detection of low-levels of message coding for the above-mentioned markers. Following manufacturer's instructions, RNA isolation was done with a QiaShredder kit (Qiagen) on isolated sprouts (scooped out of MATRIGEL™ biological cell culture substrate) followed by use of the RNAeasy kit (Qiagen), and the RT-reaction was conducted using a SMART cDNA kit (Clontech) and the RT-PCR protocol, as described in Hamdi et al., Biochem Biophys Res Commun. 295(3):668–72 [Jul. 19, 2002] but using approx. 50 ng of cDNA instead of genomic DNA per PCR reaction. The following primers were used:

```
1. AML-1 forward primer
   CGTAGATGCCAGCACGAGCCGCCGCTTCACGC //;     (SEQ ID
                                             NO:1)

2. AML-1 reverse primer
   CGGGCTTGGTCTGATCATCTAGTTTCTGC //;        (SEQ ID
                                             NO:2)

3. AC166 (ALCAM) forward primer
   CCTACAGAGCAGGTGACAATACAAGTGCTGC //;      (SEQ ID
                                             NO:3)

4. AC166 (ALCAM) reverse primer
   CATAGTTTCCAGCATCCTGATAATGAAGAC //;       (SEQ ID
                                             NO:4)

5. CD-34 forward primer
   TGCTCCTGGCCCAGTCTGAGGTGAGGCCTCAG //;     (SEQ ID
                                             NO:5)

6. CD-34 reverse primer
   GCTGAATGGCCGTTTCTGGAGGTGGCCTGGCCGGT //;  (SEQ ID
                                             NO:6)

7. AC-133 forward primer 1
   TCCAACACCGGAGGCGTCTTCCTCATGG //;         (SEQ ID
                                             NO:7)

8. AC-133 reverse primer
   CAGATAATGTTCAAAATATCCTATTATTGTTCTC //;   (SEQ ID
                                             NO:8)

9. AC-133 forward primer 2
   GAGAACAATAATAGGATATTTTGAACATTATCTG //;   (SEQ ID
                                             NO:9)

10. AC-133 reverse primer 2
    GCTTGTCATAACAGGATTGTGAATACC //.         (SEQ ID
                                             NO:10)
```

Standard immunofluorescence techniques were also employed on secondary sprouting vs. non-sprouting cells to detect higher levels of surface-expressed proteins, using specific antibodies, e.g., anti-CD34 monoclonal (Labvision); anti-CD34 polyclonal (Santa Cruz biotechnology, Inc.); anti-AC133 monoclonals 1 and 2 (Miltenyi Biotech); anti-AC166 (ALCAM) polyclonals (Santa Cruz Biotechnology, Inc.); anti-AC166 monoclonal (Antigenix America); anti-AML-1 polyclonals (Santa Cruz Biotechnology, Inc.); anti-CD31 monoclonal (Neomarkers); anti-CD62E monoclonal (Neomarkers); anti-ve-cadherin monoclonal (Chemicon); anti-CD51 monoclonal (Zymed and Chemicon); anti-survivin monoclonal (Chemicon); anti-endothelial cells monoclonal (Chemicon); anti-uPA receptor monoclonal (Neomarkers); anti-uPA polyclonal (American Diagnostica, Inc.); anti-tPA monoclonal (American Diagnostica, Inc.); anti-PAI-I monoclonal (American Diagnostica, Inc.); anti-PAI-2 polyclonal (American Diagnostica, Inc.); anti-tie-1 polyclonal (Chemicon); anti-tie-2 polyclonal (Chemicon); anti-angiopoietin-1 polyclonal (Chemicon); anti-angiopoietin-2 polyclonal (Chemicon); anti-v-CAM monoclonal (Cymbus Biotechnology and Chemicon); anti-tenascin-C polyclonal (Chemicon).

Results indicated that the population of secondary sprouting cells was a novel population of endothelial cell precursors not previously described. Table 2 indicates a partial characterization of the expression pattern of the cells in the selected population. It should be noted that CD34$^+$ cells have been isolated from some secondary sprouting colonies. Further characterization of endothelial sprout cells isolated in accordance with the present invention is underway.

TABLE 2

Markers expressed by cells selected from secondary sprouting colonies on basement membrane matrix.

| Marker | Detection means | |
|---|---|---|
| | RT-PCR | Immunofluorescence |
| CD34 | negative | negative |
| AC133 | positive | positive |
| CD166 | positive | medium |
| AML-1 | positive | medium |
| CD31 | Not done | negative |
| CD62 | Not done | weak |
| V-Cad. | Not done | weak |

Treatment of secondary sprouting colonies with 10 ng/mL of PDGF-BB or FGF-2 caused a dramatic increase in the number of cells. (Castellon R., et al, Exp Eye Res. 2002. 74(4):523–35). Treatment with PDGF-BB increased the expression of the more 'primitive' markers such as AC133, CD166 and AML-1 as well as some proteases (uPA, tPA) known to be involved in matrix invasion. These changes correlated well with the secondary sprouting phenotype (self-replicating, invasive).

Cells in secondary sprouting colonies contained high telomerase activity (FIG. 10, 3rd column) when compared to the parental cells (1st column), as measured by telomerase assay (TRAP; Yang, J., et al., *Stem and germline cells are among the only cells in postnatal tissues that continue to express telomerase activity*, J. Biol. Chem. 274(37):26141–26148 [1999]; Hsiao, R. et al., *Mature endothelial cells express very low levels of telomerase and it's lost during the first five divisions in vitro*, Anticancer Res 17:827–832 [1997]; Kolquist, K A et al., Nature Genet 19:182–186 [1998] as reviewed by Chang E et al. J. Invest. Dermatol. 118:752–8. [2002]). This enzyme activity is either very low or absent in aging or differentiated cells, but it is high in precursors. (Armstrong et al., *mTert expression correlates with telomerase activity during the differentiation of murine embryonic stem cells*. Mech Dev. 2000. 97(1–2): 109–116). Telomerase activity is also high in invasive and highly proliferative cancers but not in normal adult cells. (Blasco et al., *Telomeres and telomerase*. Genes & Development. 1999. 13:2353–2359). FIG. 10 also indicates that PDGF treatment (D) of sprouting colonies under expansive culture conditions (i.e., on MATRIGEL™ biological cell culture substrate, low serum medium) increases the activity of telomerase, indicating a higher proportion of precursor cells in the treated population or the existence of a more active enzyme in the treated cells. PDGF exerts the opposite effect on differentiated endothelial cells grown under differentiative culture conditions (i.e., low or high serum medium, plastic surface without MATRIGEL™ biological cell culture substrate).

The primary mixed endothelial cell cultures appeared to be mainly composed of mature differentiated cells that die during tube collapse after being placed on reconstituted basement membrane matrix (e.g., MATRIGEL™ biological cell culture substrate). A small proportion (>5%) appeared to be endothelial precursor cells (EPCs).

I claim:

1. An in vitro method of isolating a cellular population enriched for endothelial sprout cells, from a mixed population of mammalian cells originating from a tissue sample, the method comprising:
    culturing the mixed population of mammalian cells, said population comprising endothelial cells, on a basement membrane matrix;
    allowing tube formation by the endothelial cells to occur on a basement membrane matrix; and, after tube collapse,
    selecting, from a collapsed tube on the basement membrane matrix, at least one viable endothelial sprout cell expressing one or more elongated morphological processes.

2. The method of claim 1, wherein said mixed population of mammalian culturing is carried out with an angiogenic growth factor.

3. The method of claim 2, wherein the angiogenic growth factor is (PDGF)-BB.

4. The method of claim 1, wherein the first endothelial sprout cell further expresses one or more physiological and/or immunological feature of endothelial precursor cells.

5. The method of claim 4, wherein the physiological and/or immunological feature is a marker AC133.

6. The method of claim 4, wherein the physiological and/or immunological feature is overexpression of telomerase compared to normal differentiated endothelial cells.

7. The method of claim 1, wherein the one or more elongated morphological processes are about 50 to about 500 micrometers long.

8. The method of claim 1, further comprising:
    subculturing the at least one viable first endothelial sprout cell, under differentiative culture conditions, on a surface other than a basement membrane matrix, to obtain a population of non-proliferating endothelial cells;
    then further subculturing at least one of the non-proliferating endothelial cells that were previously subcultured under differentiative culture conditions, under expansive culture conditions on a fresh basement membrane matrix;
    allowing tube formation to occur under the expansive culture conditions; and, after tube collapse,
    selecting, from a second collapsed tube, at least one viable second endothelial sprout cell expressing one or more elongated morphological processes.

9. The method of claim 8, wherein the second endothelial sprout cell further expresses one or more physiological and/or immunological feature of endothelial precursor cells.

10. The method of claim 9, wherein the physiological and/or immunological feature is a marker selected from the group consisting of AC133, CD166, AML-1, uPA, and tPA.

11. The method of claim 9, wherein the physiological and/or immunological feature is overexpression of telomerase compared to normal differentiated endothelial cells.

12. The method of claim 8, wherein the one or more elongated morphological processes are about 50 to about 500 micrometers long.

* * * * *